United States Patent [19]
Milliman et al.

[11] Patent Number: 6,077,231
[45] Date of Patent: Jun. 20, 2000

[54] APPARATUS AND METHOD FOR LOCALIZING AND REMOVING TISSUE

[75] Inventors: Keith L. Milliman, Bethel; Mitchell J. Palmer, New Milford; Lisa W. Heaton, Norwalk; Joseph M. DeVivo, Ridgefield, all of Conn.

[73] Assignee: United States Surgical Corporation, Norwalk, Conn.

[21] Appl. No.: 08/971,539

[22] Filed: Nov. 17, 1997

Related U.S. Application Data

[63] Continuation-in-part of application No. 08/665,176, Jun. 14, 1996, Pat. No. 5,782,775.

[51] Int. Cl.$^7$ .................................................... A61B 5/00
[52] U.S. Cl. .................................................... 600/567
[58] Field of Search ........................... 600/562, 564–567; 606/130

[56] References Cited

U.S. PATENT DOCUMENTS

| | | |
|---|---|---|
| 1,568,008 | 12/1925 | Thomas . |
| 1,609,456 | 12/1926 | Boyle . |

(List continued on next page.)

FOREIGN PATENT DOCUMENTS

| | | |
|---|---|---|
| 9309720 | 11/1992 | European Pat. Off. . |
| 2610508 | 10/1987 | France . |
| 2919009 | 11/1979 | Germany . |
| 263228 | 8/1987 | Germany . |
| 4216694 | 12/1992 | Germany . |
| 534505 | 6/1970 | Switzerland . |

OTHER PUBLICATIONS

Ismet Hallac, M.D., "A New Design in Biopsy Needles", May 10, 1961, pp. 515–517.
Acuflex Microsurgical, Inc., Product Brochure, 1994.

*Primary Examiner*—Max Hindenburg

[57] ABSTRACT

A surgical apparatus for securing a needle extending therethrough includes a post having a channel therein mounted to a base. The post is positioned in operative alignment with the needle mounted on the base. A locking member is associated with the post in operative alignment with the needle. The locking member defines an opening therethrough to receive the needle, and the locking member is operable between a needle receiving position wherein the needle may be inserted or removed from the locking member and a needle retaining position wherein the needle is retained in at least one direction of movement. A method for surgically localizing and removing tissue includes the steps of providing a tissue cutting member mounted on a base and defining an opening near a distal end, the tissue cutting member further forming a tissue receiving cavity in communication with the opening, a needle disposed within the cavity and defining a longitudinal passageway therethrough, a post mounted on the base and a locking member mounted on the post and defining having a needle receiving opening in operative alignment with the needle, the locking member being operable between a needle receiving position wherein the needle may be inserted or removed from the locking member and a needle retaining position wherein the needle is retained in at least one direction of movement, locking the needle within the locking member by rotating the locking member into the needle retaining position, positioning the needle within target tissue, severing the tissue to be removed and removing the severed tissue from a patient.

16 Claims, 28 Drawing Sheets

U.S. PATENT DOCUMENTS

| | | |
|---|---|---|
| 2,117,278 | 5/1938 | Ainsworth . |
| 2,541,542 | 2/1951 | Perez et al. . |
| 3,173,414 | 3/1965 | Guillant ................. 128/2 |
| 3,470,867 | 10/1969 | Goldsmith . |
| 3,477,423 | 11/1969 | Griffith . |
| 3,561,429 | 2/1971 | Jewett ................. 128/2 |
| 3,605,721 | 9/1971 | Hallac . |
| 3,628,524 | 12/1971 | Jamshidi . |
| 4,099,518 | 7/1978 | Baylis et al. . |
| 4,174,715 | 11/1979 | Hasson . |
| 4,306,570 | 12/1981 | Matthews ................. 128/754 |
| 4,445,517 | 5/1984 | Feild ................. 128/752 |
| 4,461,305 | 7/1984 | Cibley ................. 128/754 |
| 4,651,752 | 3/1987 | Fuerst ................. 128/754 |
| 4,669,473 | 6/1987 | Richards et al. . |
| 4,678,459 | 7/1987 | Onik et al. ................. 604/22 |
| 4,741,330 | 5/1988 | Hayhurst . |
| 4,776,346 | 10/1988 | Beraha et al. ................. 128/754 |
| 4,785,826 | 11/1988 | Ward ................. 128/754 |
| 4,790,329 | 12/1988 | Simon ................. 128/749 |
| 4,817,631 | 4/1989 | Schnepp-Pesch et al. ................. 128/753 |
| 4,850,373 | 7/1989 | Zatloukal et al. ................. 128/749 |
| 4,881,550 | 11/1989 | Kothe ................. 128/752 |
| 4,926,877 | 5/1990 | Bookwalter ................. 128/754 |
| 4,931,059 | 6/1990 | Markham ................. 606/185 |
| 4,940,061 | 7/1990 | Terwilliger et al. ................. 128/754 |
| 4,958,625 | 9/1990 | Bates et al. ................. 128/754 |
| 4,971,067 | 11/1990 | Bolduc et al. ................. 128/751 |
| 4,989,614 | 2/1991 | Dejter, Jr. et al. ................. 128/752 |
| 5,021,059 | 6/1991 | Kensey et al. ................. 606/213 |
| 5,036,860 | 8/1991 | Leigh et al. ................. 128/754 |
| 5,111,828 | 5/1992 | Kornberg et al. ................. 128/754 |
| 5,127,419 | 7/1992 | Kaldany ................. 128/754 |
| 5,133,360 | 7/1992 | Spears ................. 128/754 |
| 5,148,813 | 9/1992 | Bucalo ................. 128/754 |
| 5,197,484 | 3/1993 | Kornberg et al. ................. 128/754 |
| 5,217,435 | 6/1993 | Kring ................. 604/164 |
| 5,251,641 | 10/1993 | Xavier ................. 128/754 |
| 5,257,632 | 11/1993 | Turkel et al. ................. 128/754 |
| 5,269,809 | 12/1993 | Hayhurst et al. ................. 606/232 |
| 5,271,414 | 12/1993 | Partika et al. ................. 128/754 |
| 5,289,520 | 2/1994 | Pellegrino et al. ................. 378/37 |
| 5,290,294 | 3/1994 | Cox et al. ................. 606/108 |
| 5,353,804 | 10/1994 | Kornberg et al. ................. 128/754 |
| 5,405,321 | 4/1995 | Reeves ................. 604/44 |
| 5,409,004 | 4/1995 | Sloan ................. 128/657 |
| 5,462,062 | 10/1995 | Rubinstein et al. ................. 128/754 |
| 5,488,958 | 2/1996 | Topel et al. ................. 128/754 |

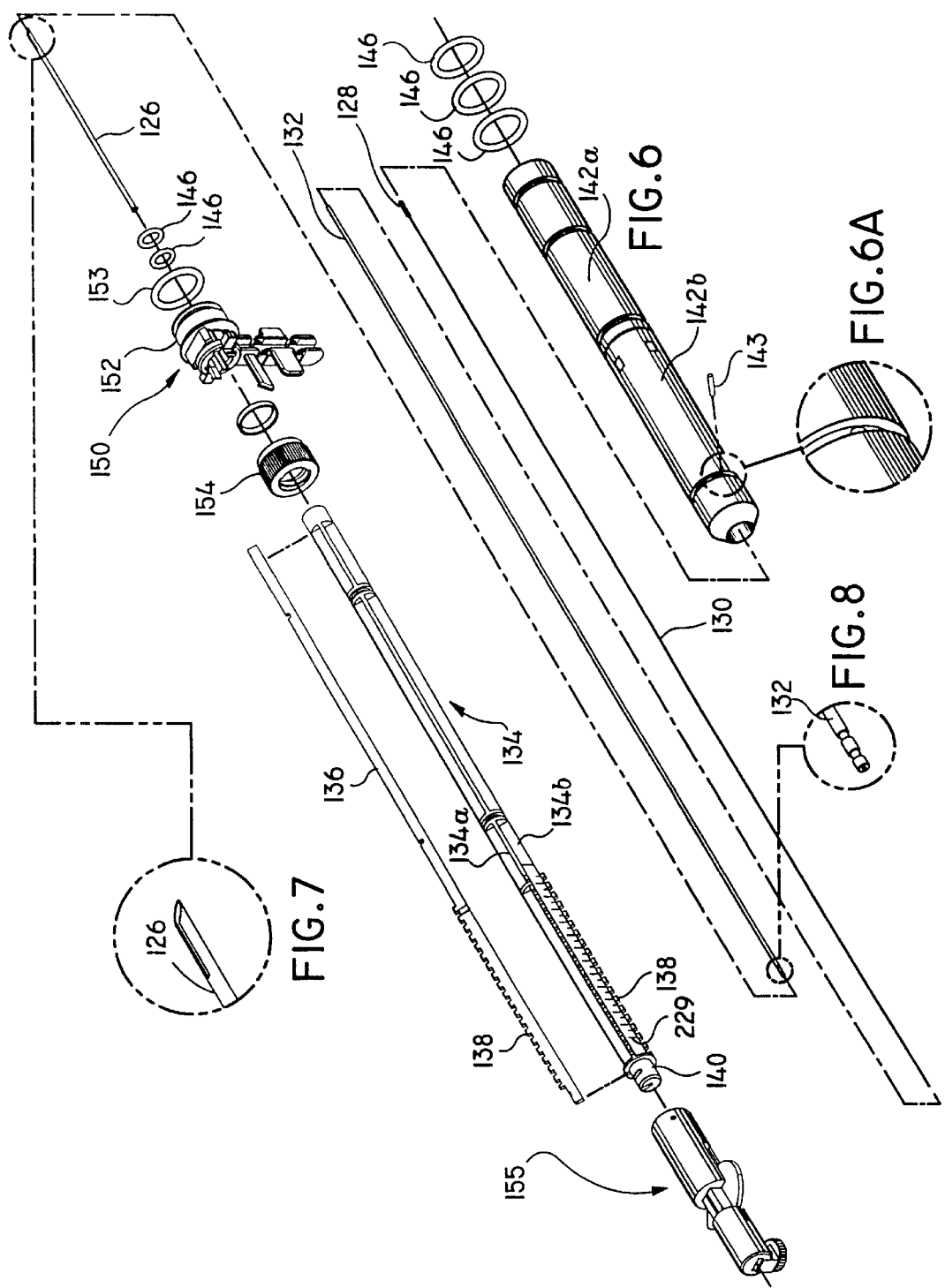

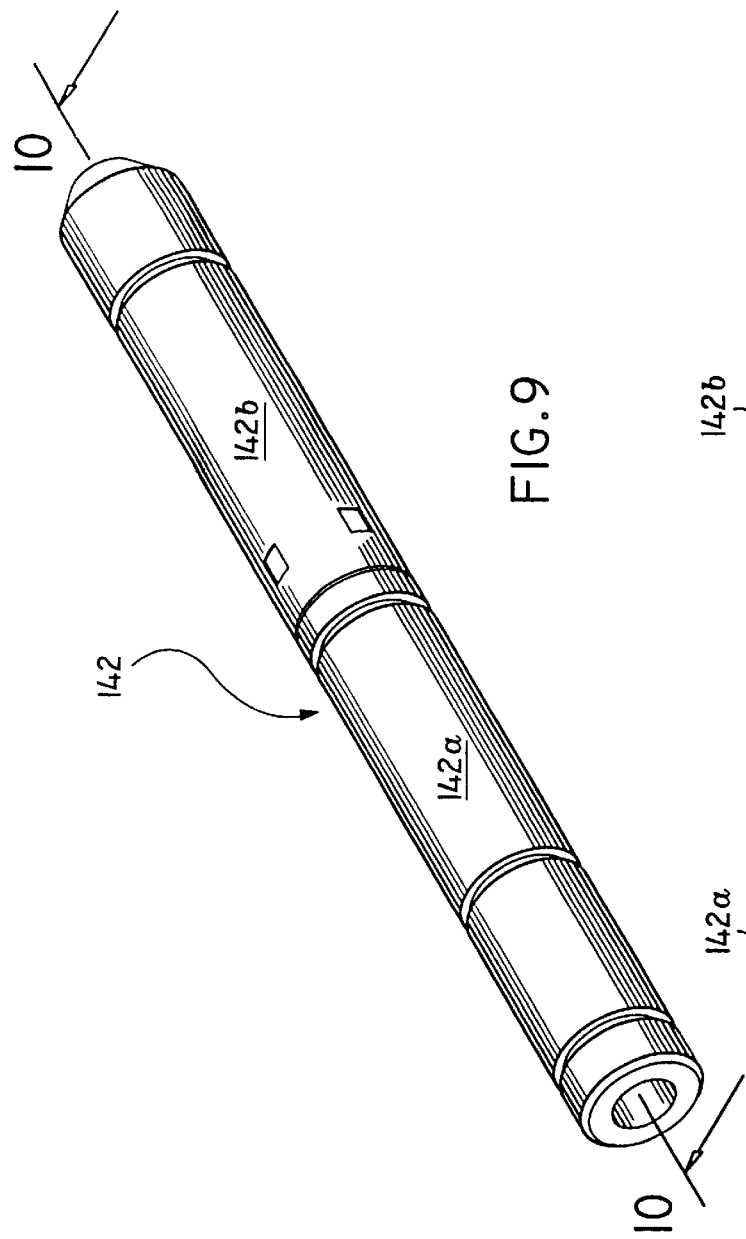
FIG. 9
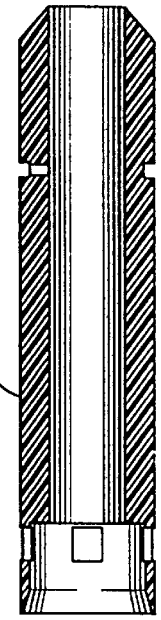
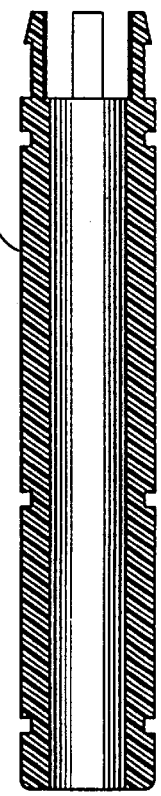
FIG. 10

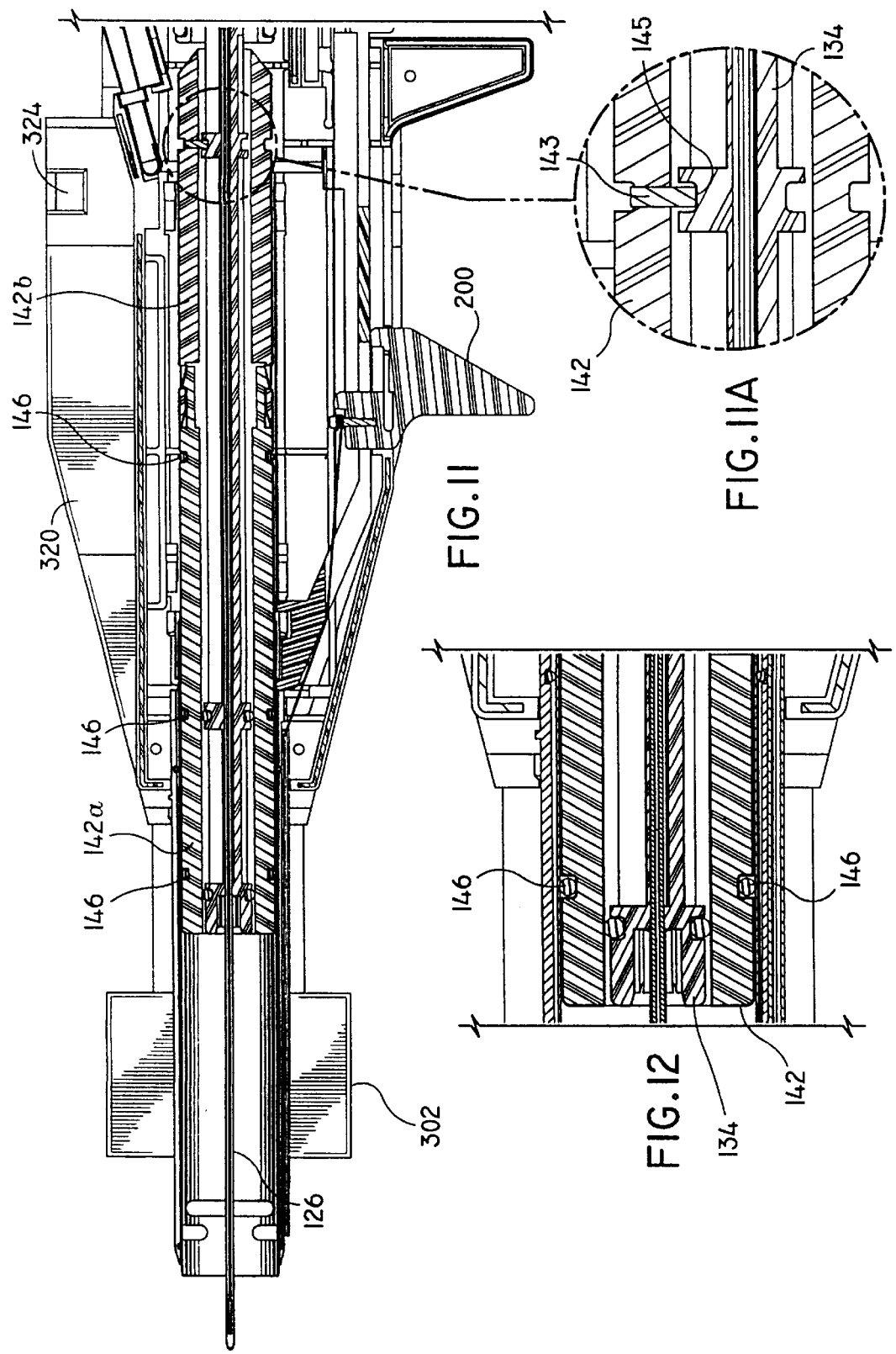

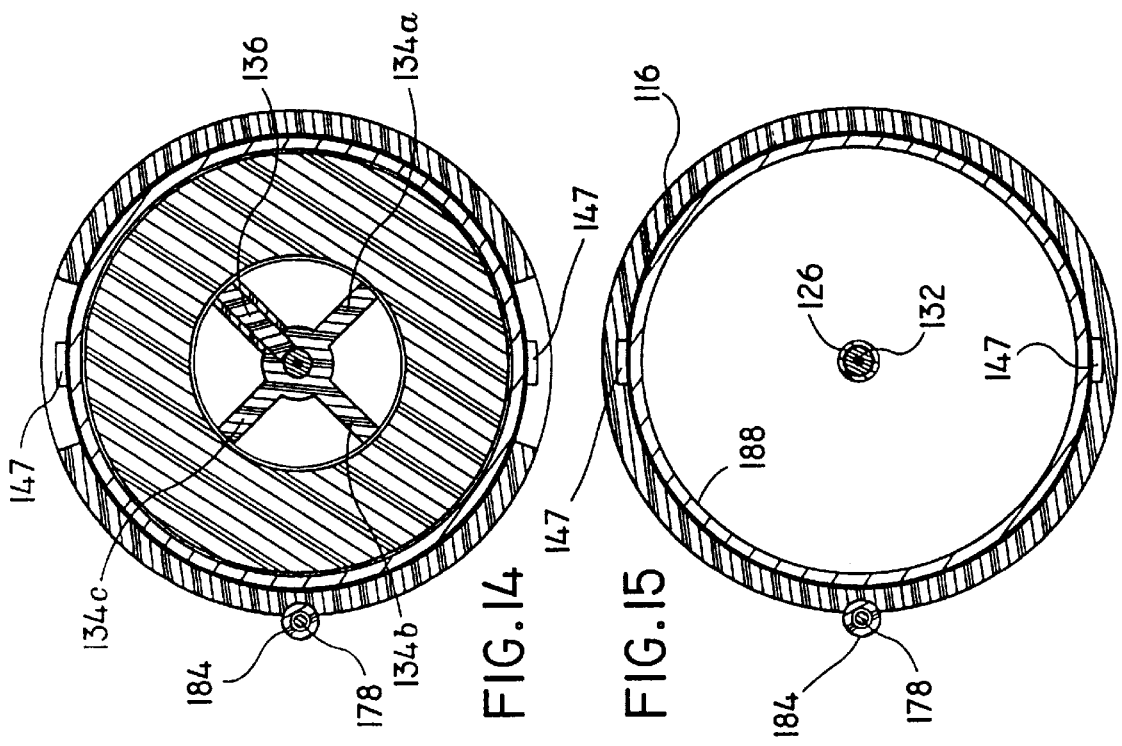
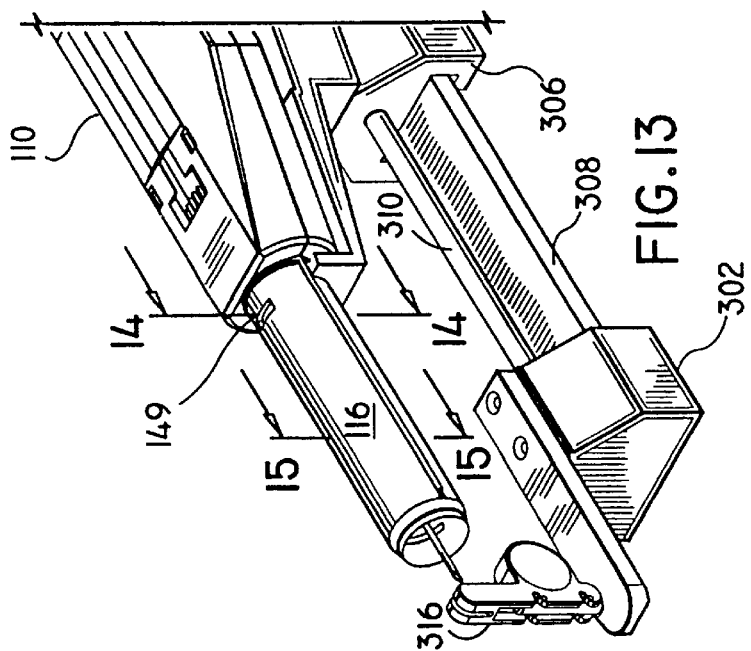

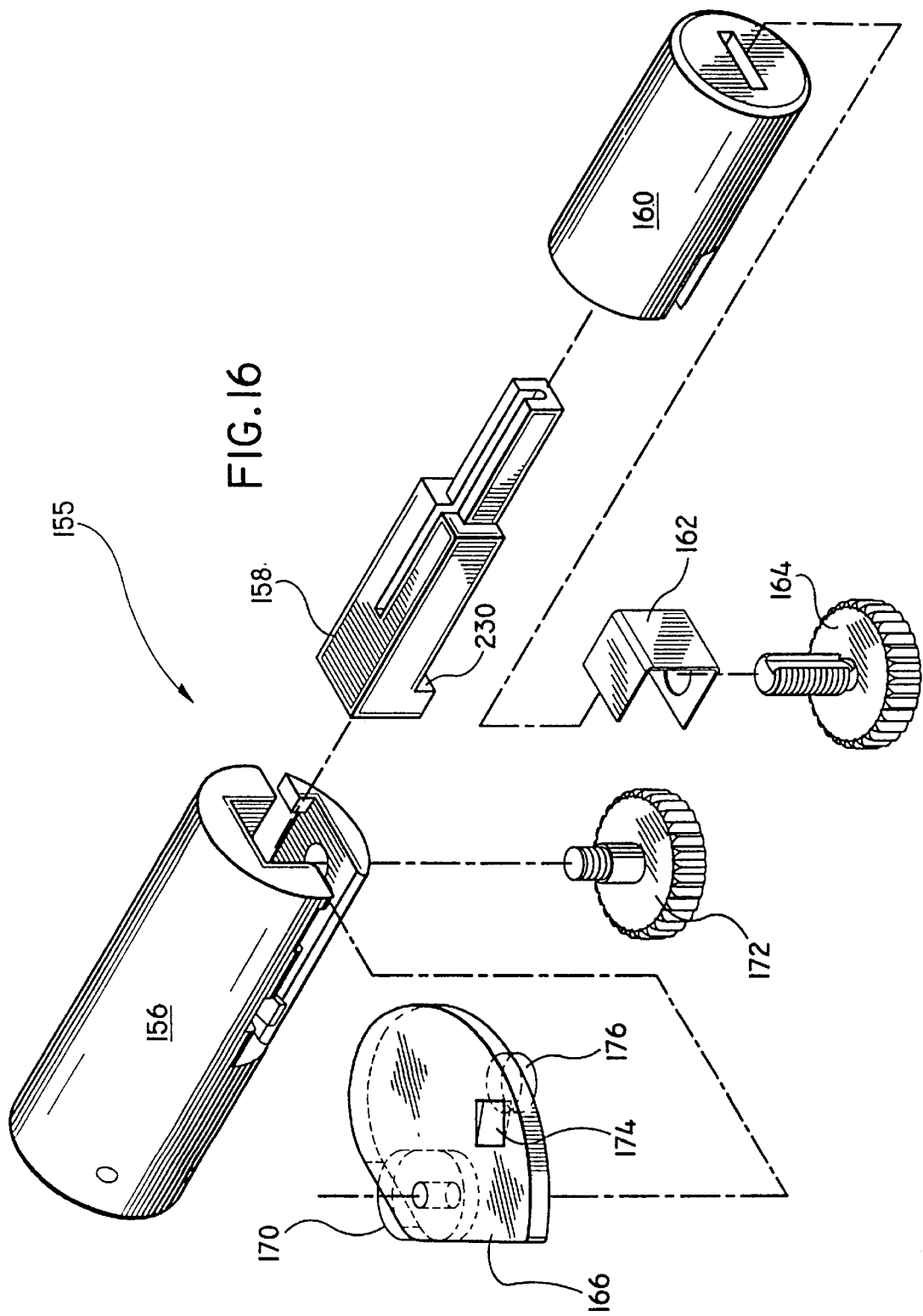

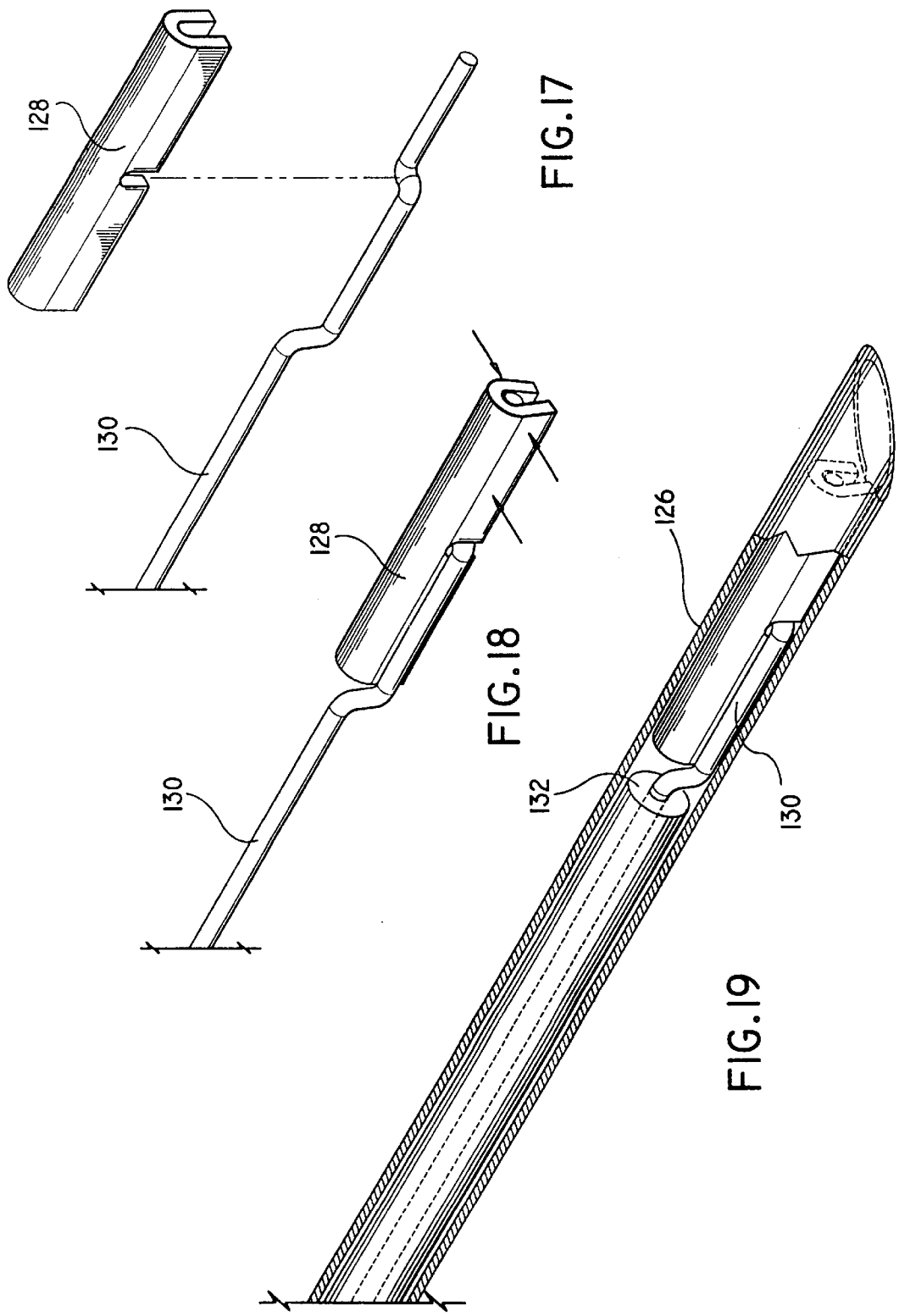

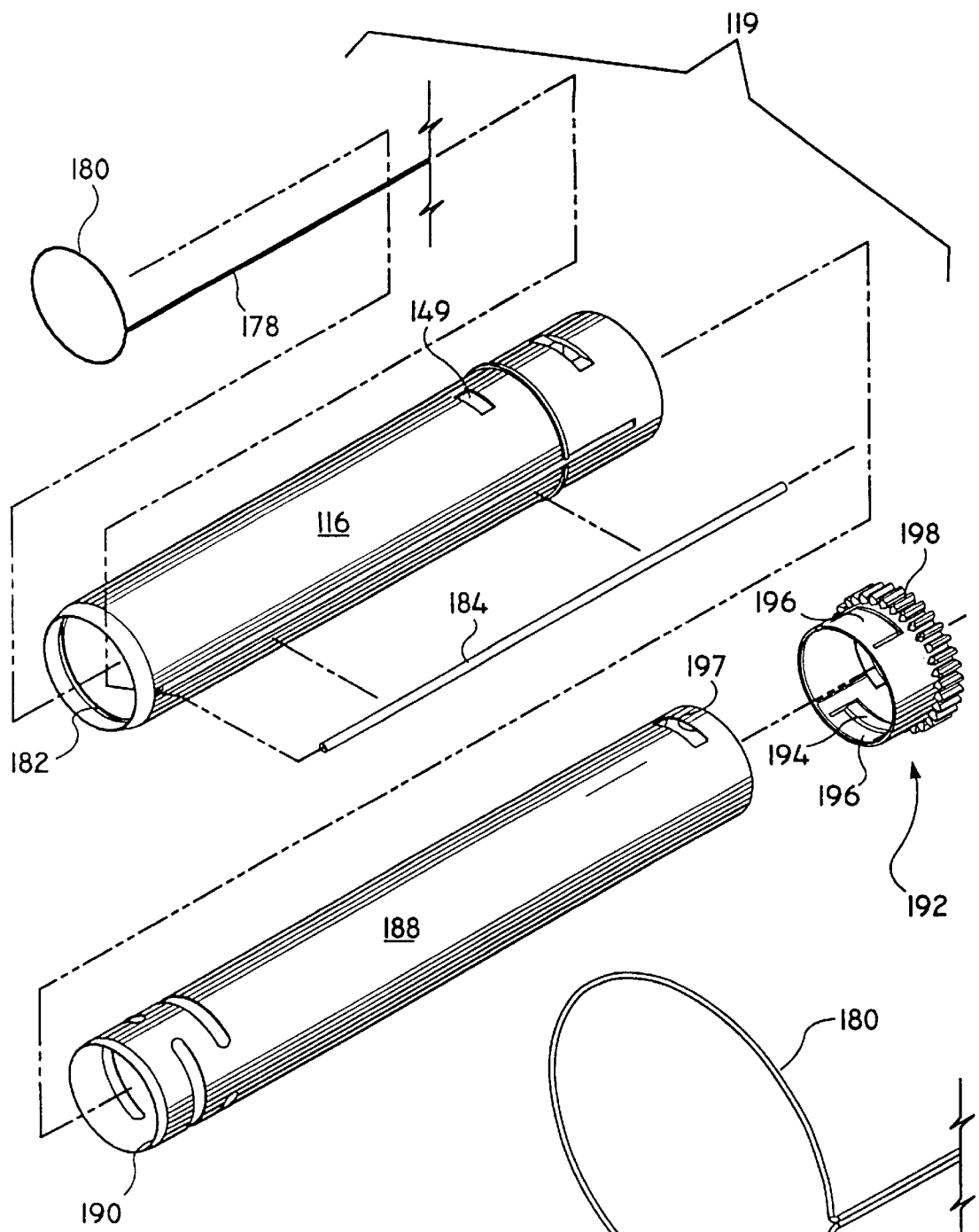

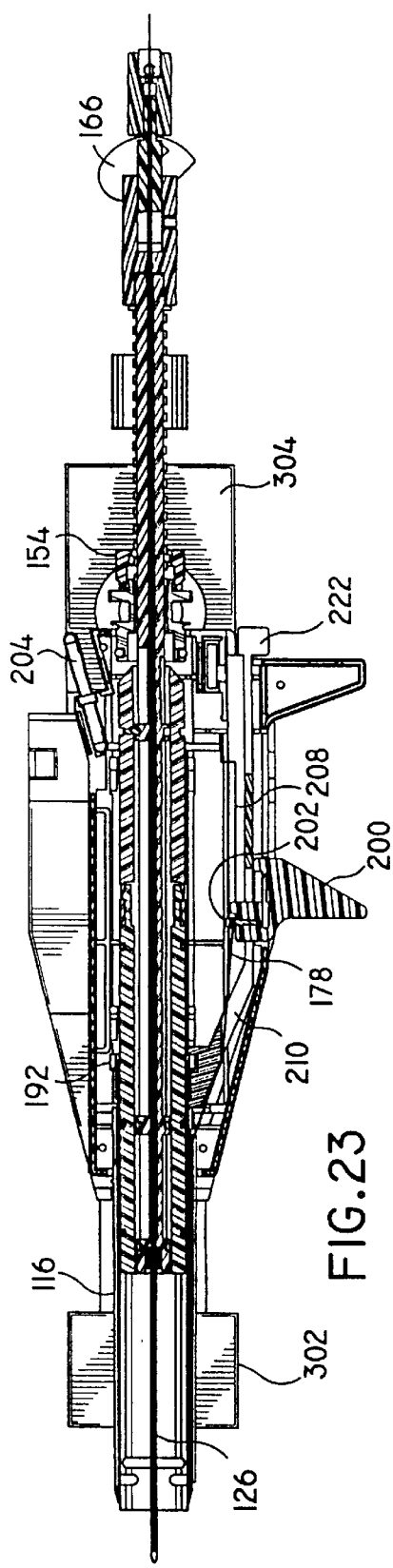
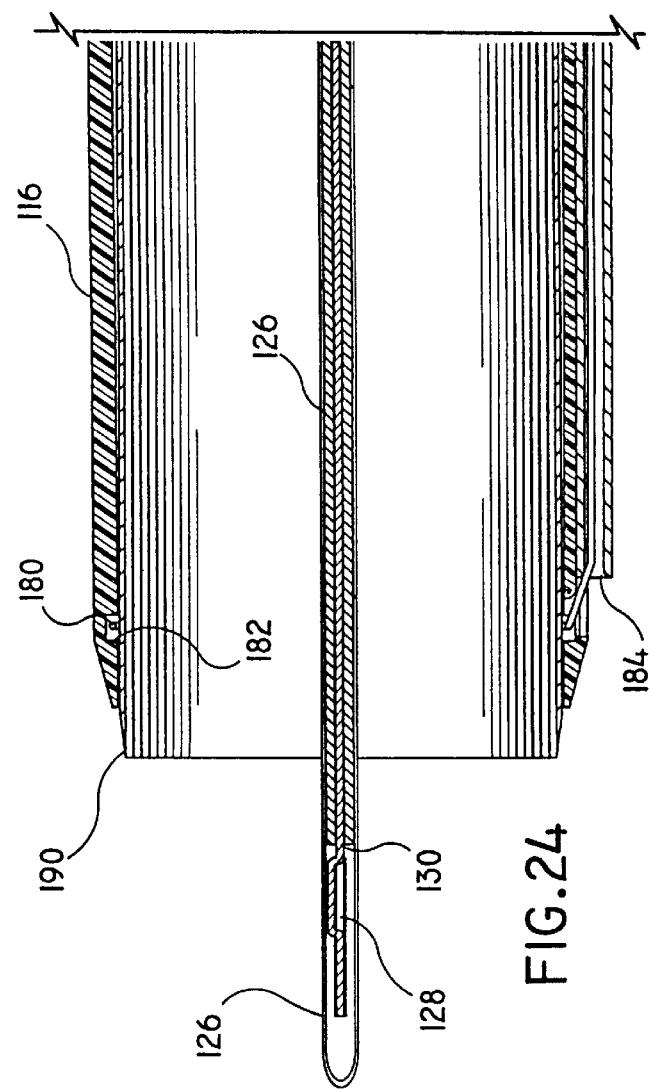
FIG.23
FIG.24

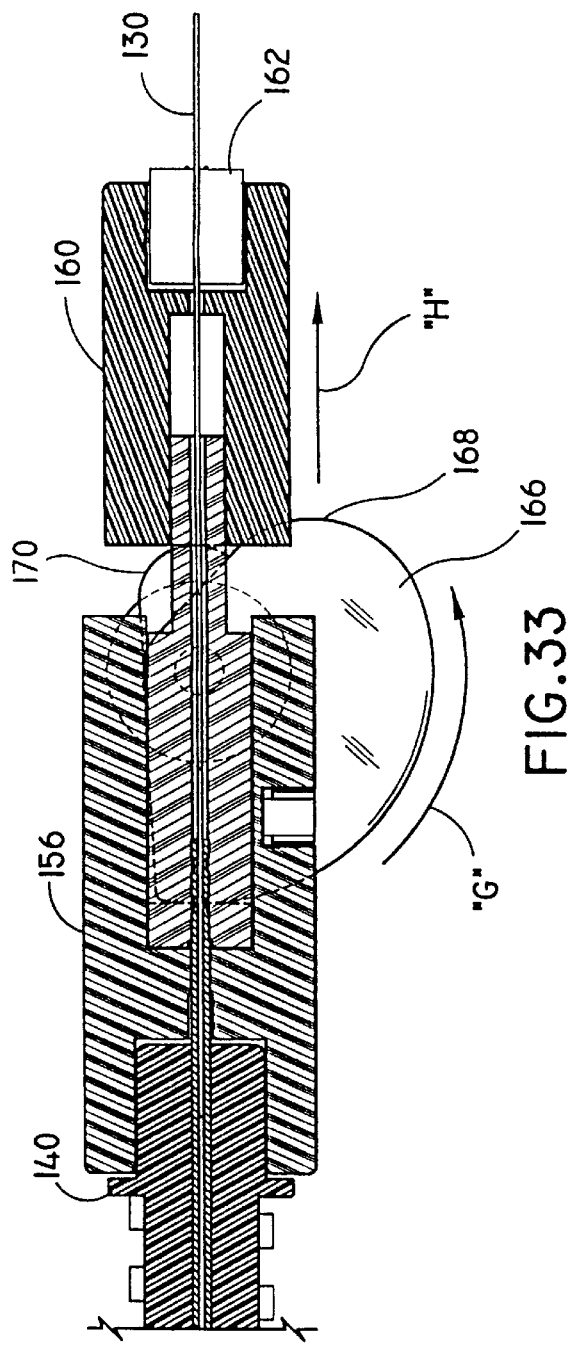
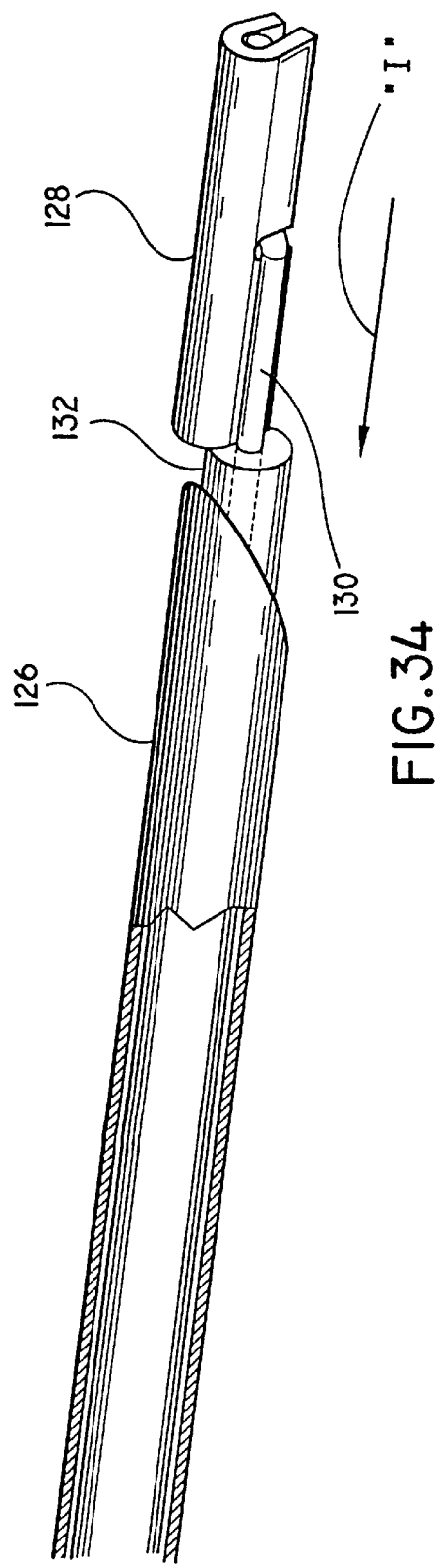

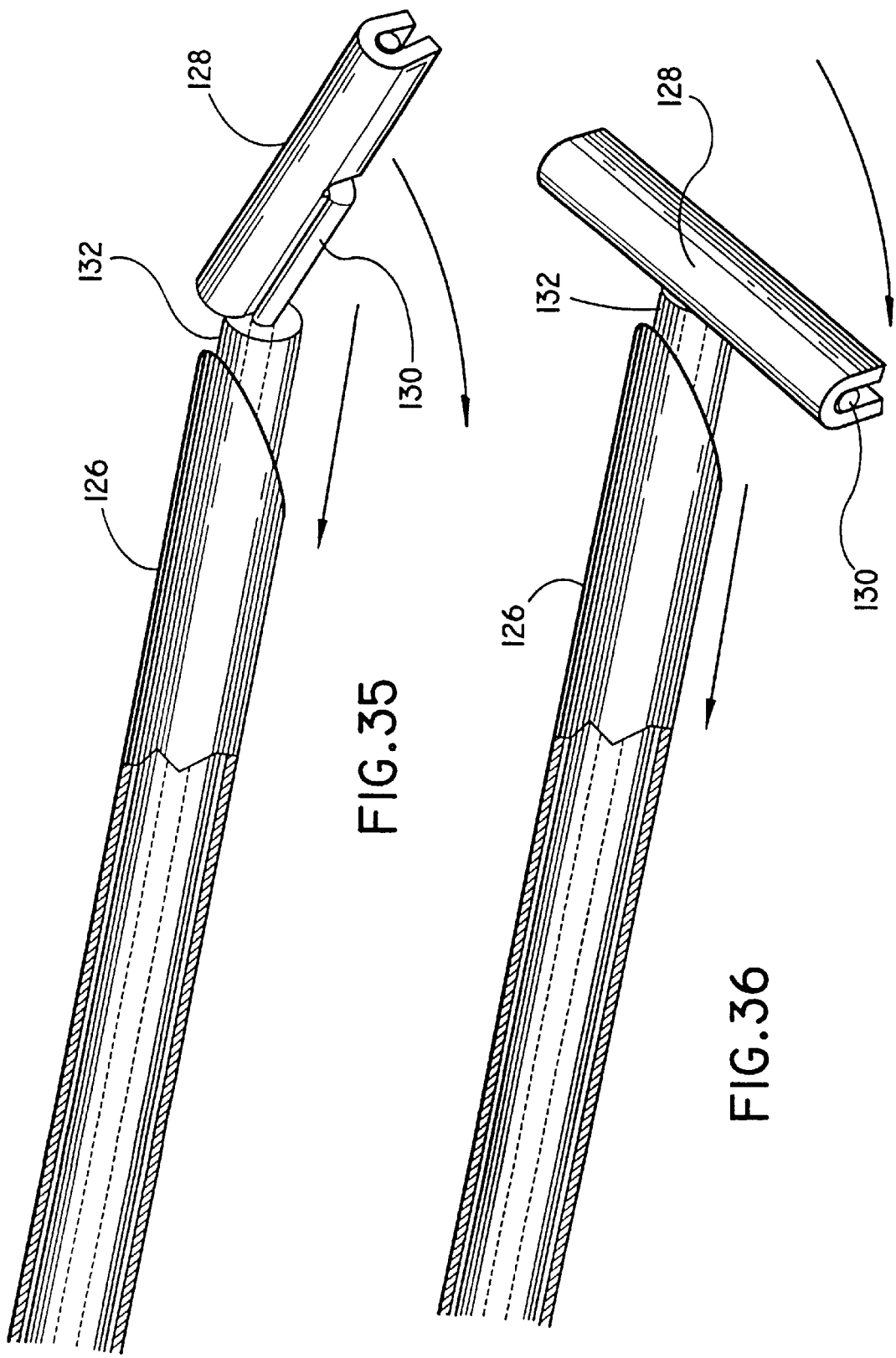

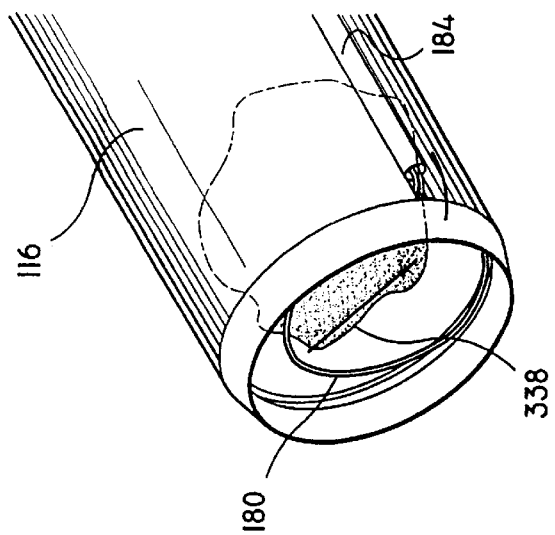
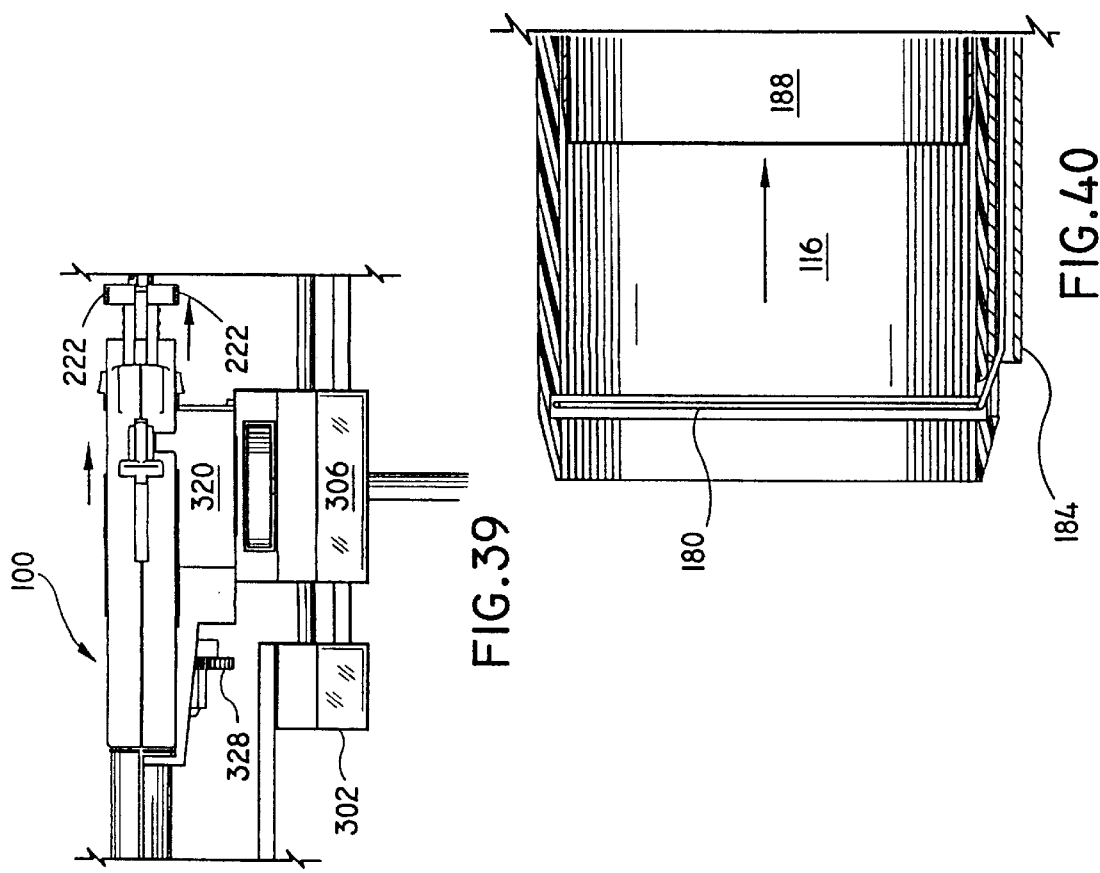

APPARATUS AND METHOD FOR LOCALIZING AND REMOVING TISSUE

CROSS REFERENCE TO RELATED APPLICATION

This application is a Continuation-in-Part of U.S. patent application Ser. No. 08/665,176 filed Jun. 14, 1996 now U.S. Pat. No. 5,782,775.

BACKGROUND

1. Technical Field

The present disclosure relates to apparatus and method for localizing and removing tissue from within a patient's body. More particularly, the present disclosure relates to apparatus and method for localizing and removing breast tissue.

2. Background of Related Art

Numerous surgical instruments have been developed for localizing either tissue that needs to be removed or a surgical incision point for biopsy and/or excision of targeted tissue. Such instruments generally determine the coordinates of the surgery site or deploy a minimally invasive surgical marker which attaches to the tissue that needs to be removed. The latter instruments generally comprise a hypodermic needle or cannula which is inserted into the body and positioned adjacent to or in contact with the targeted tissue. A cable marker is then passed through the cannula and is anchored to the target tissue thereby marking it for subsequent surgical procedure, for example, excision or biopsy. Once the lesion is localized, the cannula is usually removed from the body, leaving the cable in place protruding from the body until such a time when the biopsy or excision is performed which usually requires transporting the patient to a surgical suite.

Various tissue localization systems have been proposed to aid in locating non-palpable lesions within the body and to prevent inadvertent dislodgement and/or migration of the needle. One such system includes a cannula needle and a wire guide made of a shape memory characteristic material which assumes a J-hook configuration. Such a device may be found, for example, in U.S. Pat. No. 5,011,473 to Gatturna which discloses a needle inserted into the body and advanced to localization of a lesion. Gatturna discloses a wire which is advanced inwardly allowing a J-hooked end to engage body tissue and immobilize the needle.

A surgical apparatus and method for localizing tissue location which prevents the marker from migrating is disclosed in co-pending U.S. application Ser. No. 08/546,483. This and other tissue localization procedures greatly reduce recovery time for the patients in comparison to conventional open surgical procedures.

Instrumentation is known for removal of tissue, particularly suspect tissue within the breast of a patient, once the tissue has been localized with a guide wire. Examples of such instrumentation is disclosed in U.S. Pat. Nos. 5,111,828; 5,197,484; and 5,353,804 each of which issued to Kornberg et al. Such devices, however, require that the localization needle be inserted prior to the insertion of the biopsy device.

As is quite often the case, lesions within the breast are non-palpable, therefore, making cancerous lesions more difficult to diagnose. Early diagnosis of suspect lesions in a patient's breast, however, has been greatly enhanced through the development of imaging machines, for example, stereotactic mammography imaging systems (hereafter referred to as "stereotactic machines"). In such machines, an elongated prone supporting examining table for x-ray mammography is provided with a central breast receiving aperture, through which the patient's pendulant breast is exposed to a horizontal beam of x-rays from a source which is angularly movable through an arc centered on the patient's breast. Thus, x-ray projection through more than 360 degrees around the patient's body is possible. An example of such a stereotactic machine is disclosed in U.S. Pat. No. 5,289,520 which issued on Feb. 22, 1994 to Pellegrino et al., the contents of which are hereby incorporated by reference.

Fine needle biopsy is also facilitated by stereotactic machines. In such procedures, doctors can take advantage of the precision instrument positioning and suspect tissue position locating capabilities of the machine's imaging systems, to precisely insert a biopsy needle and retrieve a tissue sample.

The advantages of utilizing minimally invasive instruments and procedures to perform biopsy or excision of tissue are clear. For example, damage to tissue surrounding the operative site is greatly reduced and hospital stays and follow up visits are also reduced. The enormous success of such instruments in procedures such as gall bladder removal and hernia repair has led to increased development of minimally invasive instruments for other operative procedures as well.

A need exists, however, for improved minimally invasive instrumentation and methods to localize and efficiently and efficaciously biopsy and/or remove tissue in the same surgical procedure so as to avoid following up with open surgical techniques if at all possible. The present disclosure provides a combined surgical localization and minimally invasive tissue removal apparatus which is relatively easy to use and inexpensive to reliably manufacture and use.

SUMMARY

The present disclosure provides surgical apparatus and methods which address limitations associated with conventional tissue localization and removal apparatus and methods. The presently disclosed surgical apparatus and methods satisfy the need for improved minimally invasive instruments and methods to localize and efficiently and efficaciously remove tissue.

In particular, the present disclosure provides a surgical apparatus for localizing and removing tissue which includes (a) a housing defining an opening at a distal end, the housing further forming a tissue receiving cavity in communication with the opening, (b) a localizing needle movably positioned within the cavity and defining a longitudinal passageway therethrough, (c) a tissue marker movably positioned within the longitudinal passageway, (d) a marker deploying mechanism operatively connected to the marker, and (e) a tissue cutting member movably positioned adjacent the housing in proximity to the opening.

In a preferred embodiment, the marker deploying mechanism includes an actuator operatively connected to the marker, such that movement of the actuator to a first position effectuates movement of the marker in a first direction to a first position and movement of the actuator to a second position causes movement of the marker in a second direction to a second position. Preferably, the actuator includes a camming mechanism.

A further feature preferably provided as part of the marker deploying mechanism is an adjustment member operatively associated with the localizing needle, the adjustment member being movable to a predetermined position to substantially limit the insertion depth of the localization needle.

A clamping mechanism configured and dimensioned to removably attach and align the apparatus with respect to another surgical device, e.g., a stereotactic machine, is also provided which increases the versatility and performance of the presently disclosed apparatus.

The marker deploying mechanism may also include a locking mechanism operatively associated with the localization needle which is movable from a first position to maintain the localization needle in a fixed position relative to the housing, to a second position wherein the localization needle is movable relative to the housing.

The present disclosure also provides for connecting the tissue cutting member electrically to a conductive member which extends from the housing to facilitate the use of electrocautery, for example.

In an alternative embodiment, the present disclosure provides a surgical apparatus for localizing tissue, which includes (a) a housing defining a longitudinal channel therethrough configured and dimensioned to receive surgical instrumentation therein, (b) an elongated body which extends from the housing and forms an opening at a distal end, the elongated body further forming a tissue receiving cavity in communication with the opening, (c) a localization needle defining a longitudinal passageway therethrough, (d) a tissue marker movably positioned within the longitudinal passageway, and (e) a marker deploying mechanism which includes an actuator operatively connected to the marker, such that movement of the actuator to a first position effectuates movement of the marker in a first direction to a first position and movement of the actuator to a second position causes movement of the marker in a second direction to a second position.

The present disclosure further provides a method for surgically localizing and removing tissue which includes the steps of (a) providing a tissue localizing and removing instrument including a housing having a tissue receiving cavity at a distal end, a tissue localization needle operatively connected to the housing, a marker disposed within a longitudinal passageway of the tissue localization needle, and a tissue cutting member operatively connected to the housing, (b) positioning the tissue localization needle within target tissue, (c) deploying the marker to mark the target tissue, (d) severing the tissue to be removed, and (e) removing the severed tissue from the patient. The disclosed method also preferably includes the use of a stereotactic machine to obtain x-ray images of the target tissue location relative to the tissue localizing and removing instrument at various stages in the surgical procedure.

A surgical apparatus for securing a needle extending therethrough includes a post having a channel therein mounted to a base. The post is positioned in operative alignment with the needle mounted on the base. A locking member is associated with the post in operative alignment with the needle. The locking member defines an opening therethrough to receive the needle, and the locking member is operable between a needle receiving position wherein the needle may be inserted or removed from the locking member and a needle retaining position wherein the needle is retained in at least one direction of movement.

A needle guide member which is connected to the post and defines a support surface which supports the locking member therein may be included. The locking member may also be rotatably supported by the needle guide member. The post may have a pin extending therefrom and the needle guide member may have a plurality of holes configured and dimensioned to receive the pin wherein at least one of the plurality of holes corresponds to the needle receiving position and at least one of the plurality of holes corresponds to the needle retaining position. The opening may be arcuate-shaped and may be disposed at a constant radial distance from a center of rotation point on the locking member.

In a preferred embodiment, a surgical apparatus for localizing and removing tissue includes a tissue cutting member mounted on a base and defining an opening near a distal end. The tissue cutting member further forms a tissue receiving cavity in communication with the opening. A needle is disposed within the cavity and defines a longitudinal passageway therethrough. A post is mounted on the base, and a locking member is mounted on the post and defining a needle receiving opening in operative alignment with the needle. The locking member is operable between a needle receiving position wherein the needle may be inserted or removed from the locking member and a needle retaining position wherein the needle is retained in at least one direction of movement.

The surgical apparatus for localizing and removing tissue may include a needle guide member which is connected to the post and defines a support surface which supports the locking member therein. The locking member may be rotatably supported by the needle guide member. A tissue marker may be disposed within the longitudinal passageway. A marker deploying mechanism may be operatively connected to the marker. The post may have a pin extending therefrom and the locking member may have a plurality of holes configured and dimensioned to receive the pin wherein at least one of the plurality of holes corresponds to the needle receiving position and at least one of the plurality of holes corresponds to a needle retaining position. The needle receiving opening may be arcuate-shaped and may be disposed at a constant radial distance from a center of rotation point on the locking member.

A method for surgically localizing and removing tissue includes the steps of providing a tissue cutting member mounted on a base and defining an opening near a distal end, the tissue cutting member further forming a tissue receiving cavity in communication with the opening, a needle disposed within the cavity and defining a longitudinal passageway therethrough, a post mounted on the base and a locking member mounted on the post and defining having a needle receiving opening in operative alignment with the needle, the locking member being operable between a needle receiving position wherein the needle may be inserted or removed from the locking member and a needle retaining position wherein the needle is retained in at least one direction of movement, locking the needle within the locking member by rotating the locking member into the needle retaining position, positioning the needle within target tissue, severing the tissue to be removed and removing the severed tissue from a patient.

The step of positioning the needle may include advancing the needle relative to the tissue cutting member in a direction toward the target tissue. The step of mounting the base on an instrument guidance system which includes a movable instrument platform may be included. A marker may be disposed within the longitudinal passageway and the step of deploying the marker to mark the target tissue may be included.

BRIEF DESCRIPTION OF THE DRAWINGS

Preferred embodiments are described herein with reference to the drawings, wherein:

FIG. 6 is a perspective view, with parts separated, of tissue localization subassembly;

FIG. 6A is an enlarged view of the indicated area of detail in FIG. 6;

FIG. 7 is an enlarged perspective view of the distal end of a localization needle;

FIG. 8 is an enlarged perspective view of the proximal end of a localization needle;

FIG. 9 is a perspective view of the spacer member of the present disclosure;

FIG. 10 is a cross section view of the spacer member of FIG. 9 with the two parts separated;

FIG. 11 is a partial cross section view of the tissue localizing and removing instrument of FIG. 1;

FIG. 11A is an enlarged view of the indicated area of detail of FIG. 11;

FIG. 12 is a partial cross section view of the tissue localizing and removing instrument of FIG. 1, which shows the distal end of the localization needle, needle advancing shaft and spacer member;

FIG. 13 is a perspective view of the distal end of the tissue localizing and removing instrument of FIG. 1;

FIG. 14 is a cross section view taken along section line 14—14 of FIG. 13;

FIG. 15 is a cross section view taken along section line 15—15 of FIG. 13;

FIG. 16 is a perspective view, with parts separated, of a tissue marker deployment actuator;

FIG. 17 is a partial perspective view, with parts separated, showing connection of a tissue marker to a localization cable;

FIG. 18 is a partial perspective view showing cooperation of the tissue marker and localization cable of FIG. 17;

FIG. 19 is a further view, similar to FIG. 18, showing the tissue localization marker and cable encased by a localization needle;

FIG. 20 is a perspective view, with parts separated, of a tissue cutting subassembly;

FIG. 21 is an enlarged perspective view of a cutting wire loop distal end;

FIG. 23 is a longitudinal cross-sectional view of the tissue localizing and removing instrument of FIG. 1 as mounted on the cooperative portion of a stereotactic imaging machine;

FIG. 24 is an enlarged longitudinal cross-sectional view of the distal end of the presently disclosed tissue localizing and removing instrument;

FIG. 33 is a cross-sectional view, similar to FIG. 31, showing rotation of the marker deployment actuator to draw the marker towards the distal end of the localization needle;

FIG. 34 is a partial perspective view, similar to FIG. 32, showing tensile force being applied to the marker cable to deploy the marker;

FIG. 35 is a partial perspective view of the marker being deployed;

FIG. 36 is a partial perspective view of the marker in a fully deployed position;

FIG. 39 is a partial side view showing proximal movement of the instrument after having performed tissue excision;

FIG. 40 is a cross-sectional view of the distal end of the instrument which shows the movement of the central tubular shaft after the performance of tissue excision;

FIG. 41 is a partial perspective view which shows the distal end of the instrument showing deployment of a cutting wire loop;

DETAILED DESCRIPTION OF PREFERRED EMBODIMENTS

Figure 1:
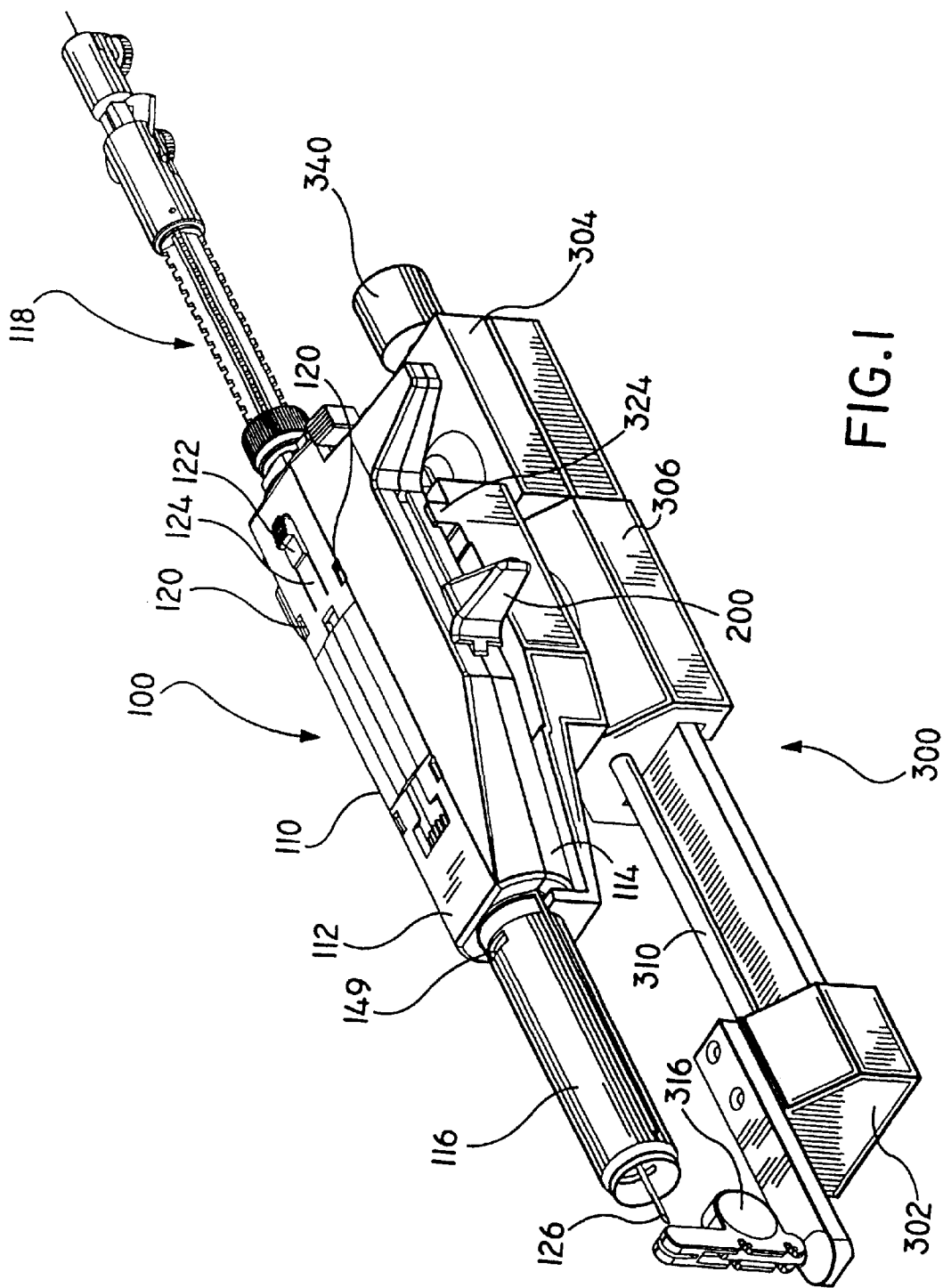
FIG. 1 is a perspective view of a tissue localizing and removing instrument constructed in accordance with the present disclosure and showing mounting structure for connection to a stereotactic imaging machine.

Referring initially to FIGS. 1–5, an instrument for localizing, removing and/or taking a biopsy of tissue in accordance with the present disclosure is designated by reference numeral 100 throughout the several views. Instrument 100 is particularly adapted for minimally invasive insertion into tissue immediately adjacent target tissue, e.g., suspect breast tissue, for localizing and removing the target tissue from the patient. Instrument 100 is also particularly adapted for mounting on a cooperative portion of an imaging machine, such as a stereotactic imaging machine. Such machines are commercially available, for example, the LORAD® StereoGuide® (trademarks of Lorad Corporation) stereotactic breast biopsy system, from Lorad Corporation of Danbury, Conn. The general structure and operational details of such a machine are disclosed in U.S. Pat. No. 5,289,520 which issued Feb. 22, 1994 to Pellegrino et al., the contents of which are hereby incorporated by reference. For purposes of clarity in the present disclosure, however, only the interactive structure between the stereotactic machine and instrument 100 will be illustrated and described herein.

Briefly, stereotactic machines facilitate stereo x-ray imaging of a patient's breast using a three dimensional (cartesian) coordinate system while the patient is in a prone position on a specially designed table. An opening is provided on the table to permit the patient's breast to be pendulantly disposed therethrough and a compression paddle having a window formed therein is used to fix the exact location of the pendulant breast relative to the operational components of the machine. Precision interaction of the instrumentation with the breast is thus facilitated, e.g, for localization and biopsy tissue removal.

It will be understood by those skilled in the art, however, that the embodiments of the tissue localization and removing instrument described herein, although generally directed to removal of breast tissue, may also be utilized for marking, removal and/or biopsy of target tissue from other areas of a patient's body as well.

As shown in FIGS. 1–5, instrument 100 generally includes a housing 110 (formed from housing half-sections 112 and 114), an elongated tubular body portion 116, which together with housing 110, hold a tissue localizing subassembly 118 and a tissue cutting subassembly 119 (FIG. 20). Except where noted otherwise, the materials utilized in the components of instrument 100 generally include such materials as polycarbonate for housing sections and related components, and stainless steel for components which transmit forces. One preferred polycarbonate material is available from General Electric under the tradename LEXAN.

To facilitate mounting of instrument 100 to a stereotactic machine, an instrument guidance mechanism 300, which may form part of the stereotactic machine, accommodates the presently disclosed instrument 100. For purposes of clarity, components which are separate from the instrument 100 and are principally for the mounting of instrument 100 to the stereotactic machine are designated by reference numerals of 300 to 399. However, as will be readily apparent based on the disclosure herein, the cooperative structures on instrument 100 and the stereotactic machine's instrument guidance mechanism 300 may be reconfigured so that more structure is included on instrument 100 and less on the stereotactic machine, or vice versa. All that is required is that the stereotactic machine instrument guidance mechanism 300 and instrument 100 cooperate so as to position instrument 100 as desired with respect to the target tissue.

The precision movement of instrument guidance mechanism 300 is facilitated by coordination with the imaging and position locating capabilities of the stereotactic machine. Instrument guidance mechanism 300 includes fixed end blocks 302 and 304 which remain stationary with respect to the proximal breast compression paddle of the stereotactic machine. Therefore, end blocks 302 and 304 also remain stationary with respect to the patient's breast once compression is achieved. The importance of the fixed relationship between the end blocks and the breast will be explained herein in the description of the structure and operation of tissue localizing subassembly 118.

An instrument mounting stage 306 is longitudinally movable along guide rail 308 between end blocks 302 and 304 either manually by rotating a drive shaft 310, as described herein, or by way of activating a drive motor (not shown) provided on the stereotactic machine. End blocks 302 and 304 are provided with mounting posts 312 and 314, respectively. As described in detail herein, post 314 provides a fixed anchor point for the localization needle with respect to the target tissue and post 312 provides a mounting surface for a needle guide 316 which is preferably provided in the same packaging along with the instrument 100. Needle guide 316 attaches readily to post 312, e.g., by snap fitting onto the post.

Figure 25:
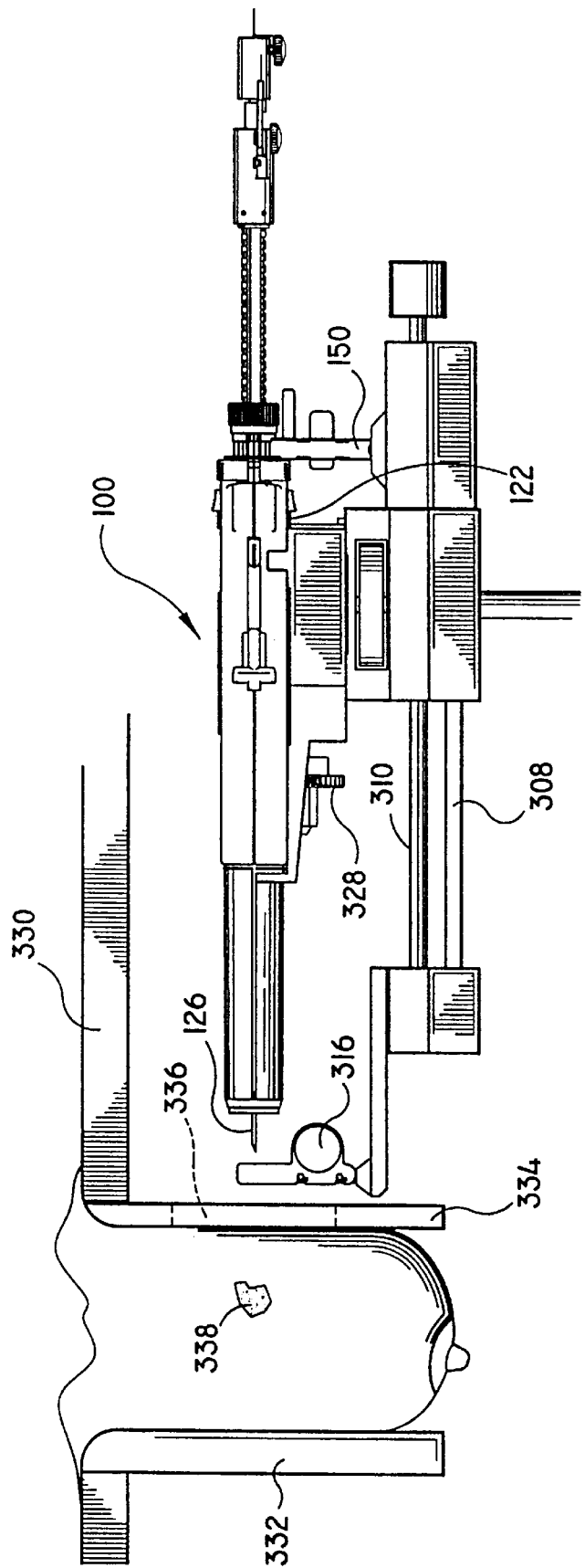
FIG. 25 is a perspective view showing the instrument of FIG. 1 in use.

Instrument 100 is provided with eight rectangular mounting slots 120, four of which are formed on each side of the instrument's housing half-sections 112 and 114. Additionally, each housing half-section 112 and 114 has a stop 122 which is formed on a flexible finger 124 formed on the housing wall. Thus, instrument 100 can be securely mounted on either side by positioning instrument 100 such that slots 120 receive correspondingly located hooks 318 formed on an instrument mounting platform 320 disposed on the stereotactic machine. Thereafter, instrument 100 is simply pulled proximally until stop 122 of flexible finger 124 snaps out as it passes proximally of the end wall of platform 320 (FIG. 25). This symmetrical arrangement of mounting slots 120 and stops 122 allows instrument 100 to be oriented on platform 320 to suit the preference of the person using the instrument during a given procedure. To dismount instrument 100 from platform 320, the flexible finger 122 on the side of instrument 100 in abutment with platform 320 is pushed in to permit distal movement of instrument 100 off of hooks 318.

Figure 5:
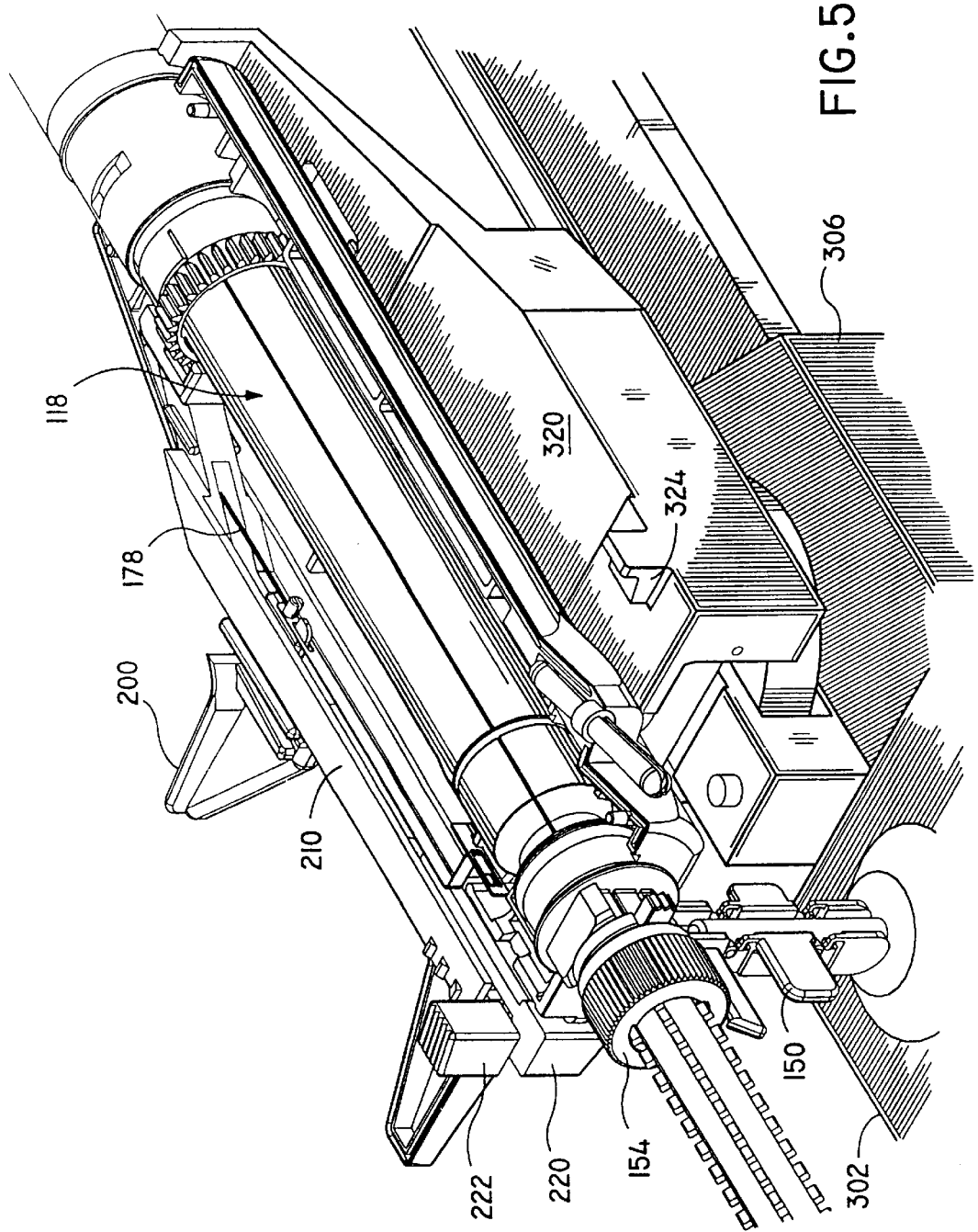
FIG. 5 is a partial perspective view of components contained in the housing with the tissue localizing subassembly positioned therein.

To further stabilize instrument 100, platform 320 is provided with a semi-circular cradle 322 disposed at the distal end of the platform and rests 324 formed near the proximal end of platform 320. Rests 324 are disposed near the outer edges of the top surface of platform 320. As illustrated in FIG. 5, depending on the orientation of instrument 100, i.e., resting on its left side or its right side, only one of rests 324 will contact and support housing 110. Collectively, the platform 320, cradle 322 and rests 324 serve to maintain longitudinal alignment of instrument 100 with the axis of insertion, hereinafter referred to as the "z-axis". Finally, platform 320 is provided with a window 326 to facilitate the coring operation of the tissue cutting subassembly 119 (FIG. 20), as will be described in detail herein.

Figure 3:
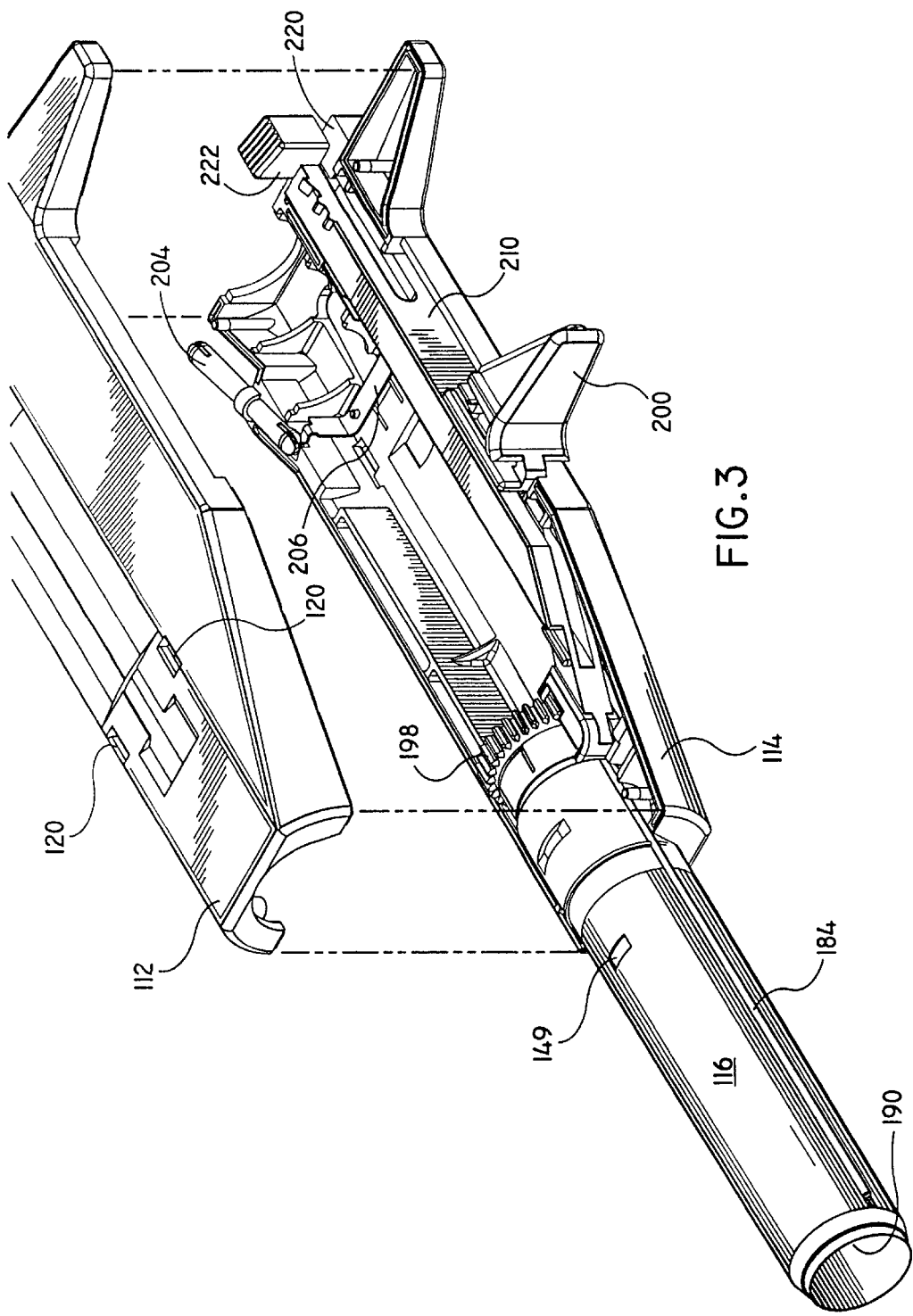
FIG. 3 is a partial perspective view, with parts separated, of components contained in a housing, without tissue localizing subassembly positioned therein.

Referring to FIG. 3, housing half-sections 112 and 114 are preferably molded to have predetermined contoured regions for housing the various components as well as facilitating the instrument's operation. Housing half-sections 112 and 114 may be joined together by any suitable means, for example, by sonic welding, snap fitting, fasteners, adhesive bonding or the like.

Figure 22:
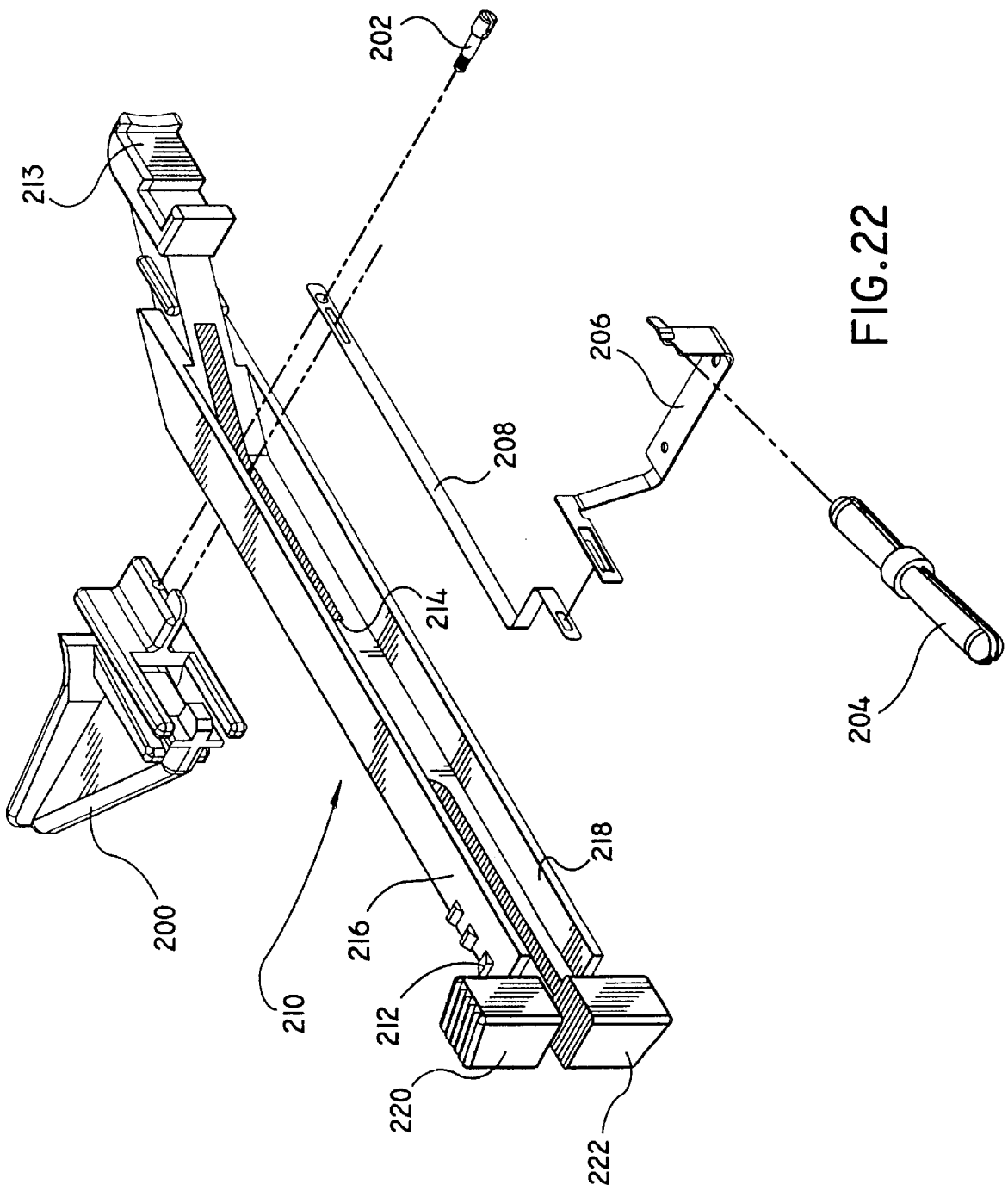
FIG. 22 is a perspective view, with parts separated, of an actuator or trigger assembly with electrocautery contacts.

The relative assembly of the various structural components of instrument 100 can be readily appreciated with reference to FIGS. 4–22. In particular, the structural components of tissue localization subassembly 118, as shown in FIGS. 4–19 and the structural components of tissue cutting subassembly 119, as shown in FIGS. 20–22, will now be described in detail.

Figure 4:
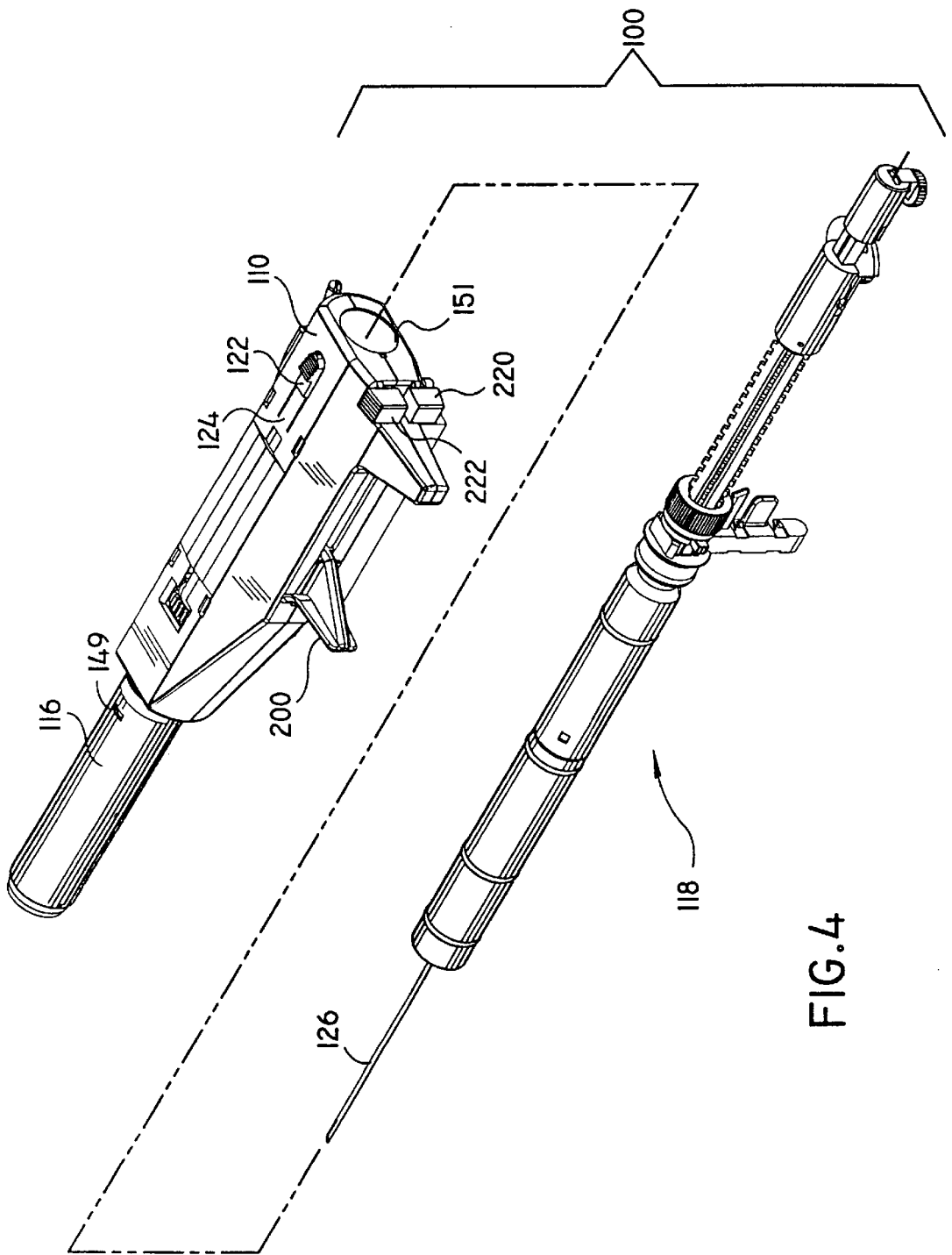
FIG. 4 is a perspective view with parts separated, of the tissue localizing and removing instrument of FIG. 1.

Referring initially to FIGS. 4 and 5, tissue localizing subassembly 118 is configured and dimensioned to be readily inserted within or removed from a longitudinal passageway formed in housing 110. Upon full insertion of tissue localizing subassembly 118, the distal end of localization needle 126 extends beyond the distal end opening of elongated tubular body portion 116 (best shown in FIG. 1).

As shown in FIGS. 6–19, tissue localization subassembly 118 includes a tissue marker 128 attached to the distal end of a wire or cable, such as cable 130, for example, by applying a crimping or swaging force, as shown in FIG. 18. Marker 128 is preferably shaped to facilitate its attachment to cable 130. For example, marker 128 may be U-shaped or tubular. The distal end portion of cable 130 is provided with a series of bends to accommodate marker 128 within the distal end of localization needle 126, as shown in FIG. 19. This offset relationship of marker 128 to cable 130 also facilitates deployment of marker 128. Cable 130 is inserted through a passageway formed by the communication of a longitudinal bore formed through hollow localization needle 126 and a longitudinal bore formed through marker advancing tube 132. The proximal end of localization needle 126 is securely inserted in an opening formed in the distal end of a needle advancing shaft 134. Preferably needle advancing shaft 134 has a longitudinal passageway formed along the entire length thereof. To facilitate assembly, a separate slat 136 is positioned in a complementary shaped opening formed along the length of shaft 134 in communication with the longitudinal passageway, as best shown in FIGS. 6 and 14. The slat 136 may be secured in place by any suitable methods, e.g., bonding, adhesives, sonic welding, etc.

A series of uniformly spaced notches 138 are formed along an outside edge near the proximal end of slat 136 and extend approximately one-third the distance along the length of the slat. Notches 138 are also formed on an outside edge near the proximal end of radially extending surfaces 134a, 134b and 134c (FIG. 14). When slat 136 is assembled to become part of shaft 134, the notches 138 formed on each of the respective surfaces 134a, 134b, 134c and slat 136 are axially offset relative to the notches 138 formed on the adjacent surface or slat. In this manner a continuous spiral path is formed peripherally about the section of shaft 134 having notches 138 formed thereon. This path serves as a thread to facilitate the precision longitudinal movement of shaft 134, as will be explained in greater detail further herein.

The portion of needle advancing shaft 134 that is distal of notches 138 is housed within a two part spacer 142 formed by molded half-sections 142a and 142b, as best shown in FIGS. 9 and 10. The half sections 142a and 142b are configured and dimensioned to readily snap fit together to form a tubular enclosure. As shown in FIGS. 6, 6A, 11, 11A, spacer member 142 is axially fixed to needle advancing shaft 134, for example by a pin 143 passing through a transverse bore formed through spacer member 142 and seated in an annular groove 145 formed on needle advancing shaft 134.

Referring to FIGS. 11 and 12, a series of O-rings 146 are fitted within peripheral axially spaced grooves formed along the outer surface of half-sections 142a and 142b. O-rings 146 may be made of any suitable compressible material, e.g., elastomeric materials, to facilitate sealing and reduce the passage of fluids from the patient into the instrument. As shown in FIGS. 13–15, to further manage and control the flow of escaping fluids from the patient, instrument 100 is provided with a pair of longitudinal passageways 147 which may be formed along the length of tubular body portion 116 as shown in FIGS. 14 and 15, in fluid communication with outlet slots 149 formed near the proximal end of tubular body portion 116 to facilitate venting of any fluids escaping from the patient through the instrument. Alternatively, longitudinal slots (not shown) may be formed along the length of coring cannula 188 which are in fluid communication with the distal end of the instrument 100 and outlet slots 149 formed through tubular body portion 116.

A needle clamp 150 (FIGS. 5 and 6) is slidably disposed around needle advancing shaft 134. A bushing 152 facilitates mounting needle clamp 150 in a circular opening 151 formed in the distal end wall of instrument housing 110 (FIGS. 4 and 5). An elastomeric O-ring 153 is seated in a peripheral groove formed on the outer surface of bushing 152. O-ring 153 provides the user with an indication of proper seating and insertion of bushing 152 in instrument housing 110.

An insertion depth adjustment knob 154 is threaded over the continuous path formed by notches 138 which as noted above, form a thread. A locking mechanism is provided on needle clamp 150 to retain adjustment knob 154 thereby preventing unintentional movement of localization needle 126. The structure and operation of the locking mechanism will be explained in detail further herein.

Figure 29:
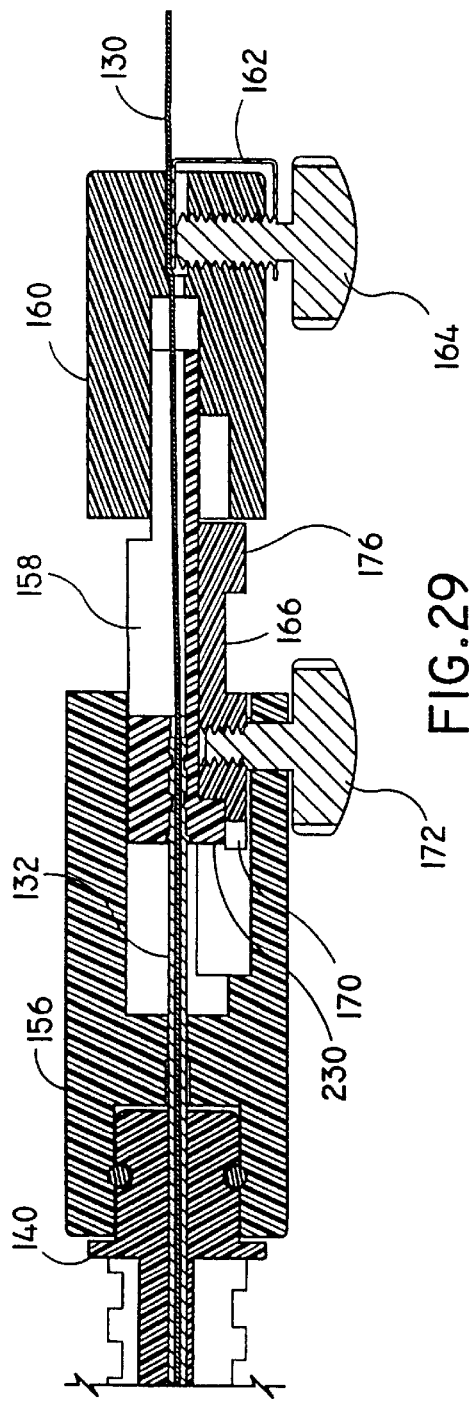
FIG. 29 is a side cross-sectional view of a section of the proximal end of the instrument which shows the tissue localization subassembly and the marker cable positioned thereon.
Figure 30:
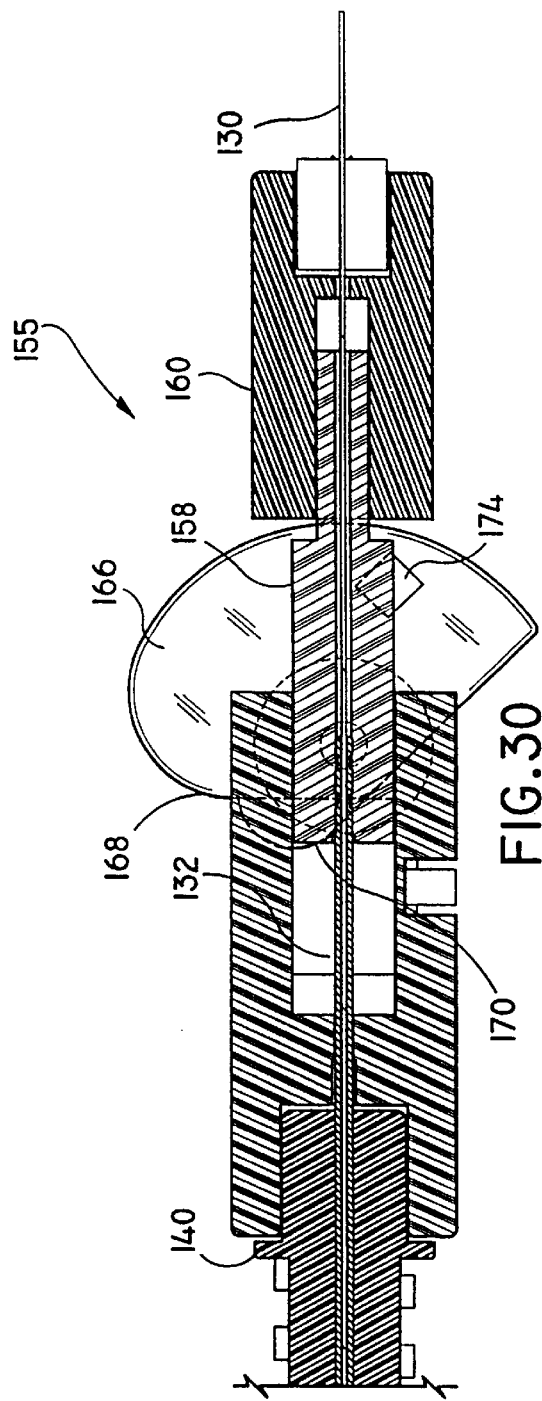
FIG. 30 is a top cross-sectional view of the proximal end of the instrument which shows a cam member in full view.

Needle advancing shaft 134, marker advancing tube 132, and cable 130 are each connected to a marker deployment mechanism 155 which will now be described with reference to FIGS. 6, 16 and 29. In particular, needle advancing shaft 134 is secured in a cylindrical actuator housing member 156 by way of end cap 140 being secured in a bore formed in the distal end of actuator housing member 156, as best seen in FIG. 29. Proximal end of marker advancing tube 132 is secured in slide member 158 which is slidably received in an opening formed in the proximal end of actuator housing member 156. Finally, cable 130 is secured to cable anchor 160 through compression applied by a set screw 164. The cable 130 is compressed between clip 162 and the inner wall of a bore formed through cable anchor 160.

Actuation of tissue marker 128 is facilitated efficaciously by a compound cam member 166 which is rotatably mounted in actuator housing member 156 by rotation knob 172. Although shown in FIG. 16 and 29 as a threaded screw, knob 172 can also be in the form of a snap fit key defining a geometry which fits into a complementary shaped opening formed in compound cam member 166. Cam member 166 has two camming surfaces 168 and 170 to effectuate deployment of tissue marker 128 at a desired position relative to the target tissue. As will be described in detail herein, operational movement of camming surface 168 causes marker advancing tube 132, marker 128 and cable 130 to be moved distally. Operational movement of camming surface 170 causes cable 130 to be pulled proximally while advancing tube 132 is maintained in its distally deployed position, thereby rotating marker 128 into position. Cam member 166 is further provided with stops 174 and 176, the function of which will become apparent in the description of the operation of the tissue localizing subassembly 118 described herein.

Tissue cutting subassembly 119, which facilitates coring of the target tissue as well as severing of the tissue from the surrounding tissue, will now be described with reference to FIGS. 20–24. A tissue cutting wire 178 is provided which has a loop 180 formed at the distal end. Loop 180 is seated in an annular groove 182 which is formed peripherally on the inner surface of elongated tubular body 116 near a distal end thereof. Cutting wire 178 passes through an opening formed through the sidewall of elongated tubular body portion 116 and travels through conduit 184. A longitudinal groove 186 is formed along the outer surface of elongated tubular body portion 116 to receive conduit 184.

Referring to FIG. 24 in conjunction with FIG. 20, a coring cannula 188 is concentrically disposed within elongated tubular body 116 such that an annular cutting edge 190 extends from the distal open end of body 116. In this manner coring cannula 188 serves the additional function of maintaining loop 180 in its pre-fired position disposed in groove 182. As best shown in FIG. 20, a collar 192 is readily assembled on coring cannula 188, for example, by sliding collar 192 over the distal end of cannula 188 such that raised tabs 194 formed on flexible fingers 196 snap into retaining slots 197 formed on coring cannula 188. Collar 192 is further provided with teeth 198 formed around the periphery of the proximal end to form a gear which facilitates rotation of coring cannula 188 during the tissue cutting operation of instrument 100 as will be described in detail herein.

Referring to FIGS. 22 and 23, tissue cutting assembly 119 preferably includes a trigger 200 which is slidably disposed between housing half-sections 112 and 114. Cutting wire 178 is attached near a proximal end thereof to trigger 200 by, for example, pin 202 which is preferably electrically conductive. As an additional feature, tissue cutting assembly 119 may be provided with electrocautery capability. Electrocautery is facilitated by electrically connecting wire 178 with an electrocautery plug 204 which is inserted in a bore formed in housing 110. Plug 204 is electrically connected to wire 178 by way of contacting jumper 206 which is connected to jumper 208 which is in turn held in place by screw 202. As noted above, screw 202 is preferably electrically conductive so as to electrically connect jumper 208 with cutting wire 178.

To enable the severing of the suspect tissue by cutting wire 178, tissue cutting assembly is preferably provided with a slide member 210. Slide member 210 serves several functions. First, stops 212 are provided near the distal end of the slide member to maintain the longitudinal position of the slide member within housing 110 by biasing against the inner surface of the proximal end wall of the housing. A cradle 213 is formed at the distal end of slide member 210 to receive the gear formed by teeth 198 of collar 192. In this manner, when slide 210 is inserted in its distal most position with stops 212 biased against the inner surface of the proximal end wall of housing 110, coring cannula is held longitudinally fixed while being enabled to rotate. This longitudinal fixing of coring cannula 188 as well as the obstacle provided by the proximal end wall of housing 110 prevents firing of trigger 200, thereby preventing premature dislodgement of cutting wire loop 180 from annular groove 182.

To enable actuation of cutting wire 178, slide member 210 is provided with leg portions 216 and 218 which flex inwardly toward each other when pressure is applied to release buttons 220 and 222 which extend transversely away from each other at the proximal end of leg portions 216 and 218, respectively. Such applied pressure will enable leg portions 216 and 218 to flex sufficiently for stops 212 to clear the circular opening formed at the proximal end of housing 110. As will become evident in the description of the operation of instrument 100, this feature enables retraction of coring cannula 188 to permit actuation of cutting wire 178.

Figure 2:
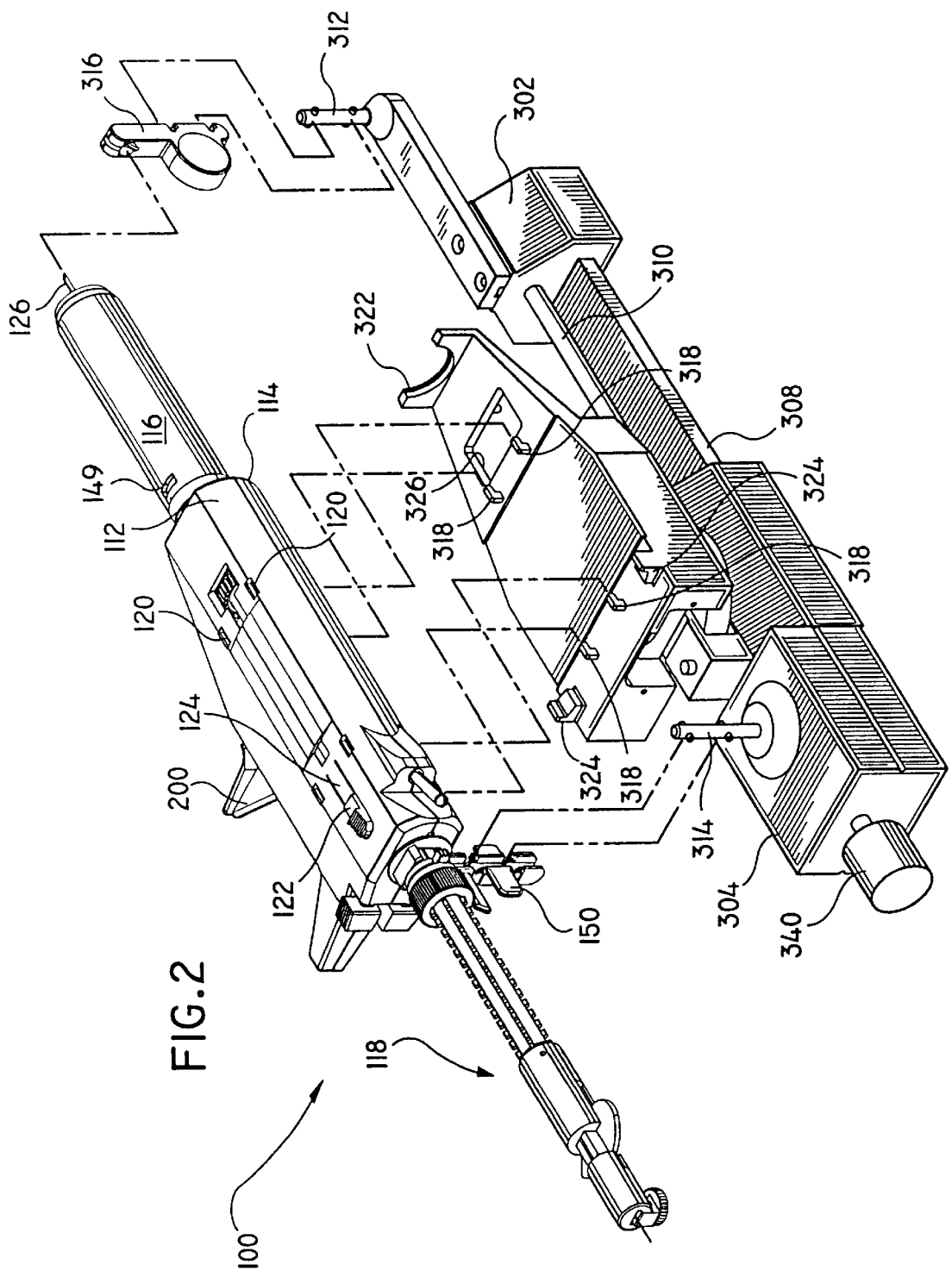
FIG. 2 is a perspective view with parts separated, from a reverse angle of FIG. 1, of the tissue localizing and removing instrument mounted on a cooperative portion of a stereotactic imaging machine.

Operation of instrument 100 as illustrated in FIGS. 25–42 will now be described in detail. In one preferred method of performing localization and removal of target tissue, instrument 100 is installed on instrument guidance mechanism 300 of a stereotactic machine (as best shown in and described herein with reference to FIG. 2) by snapping housing 110 into place over hooks 318 and by snapping needle clamp 150 on to post 314. A longitudinally movable gear 328 is slid to mesh with teeth 198 of collar 192 to enable the drive motor (not shown) of the stereotactic machine to rotate coring cannula 190. Needle guide 316, which may be provided as part of a kit with instrument 100, is snapped into place on post 312 (FIG. 2).

With instrument 100 positioned in the proximal-most position or "home" position for instrument stage 306 of the stereotactic machine, the patient lies prone on a table 330 such that the breast being examined is pendulantly positioned through an opening formed in the table surface. The opening is positioned above the operational components of the stereotactic machine such that the breast is situated between a fixed paddle surface 332 and movable compression paddle surface 334 which has a window 336 formed therein. Window 336 provides access to the breast for imaging and operative purposes.

Figure 26:
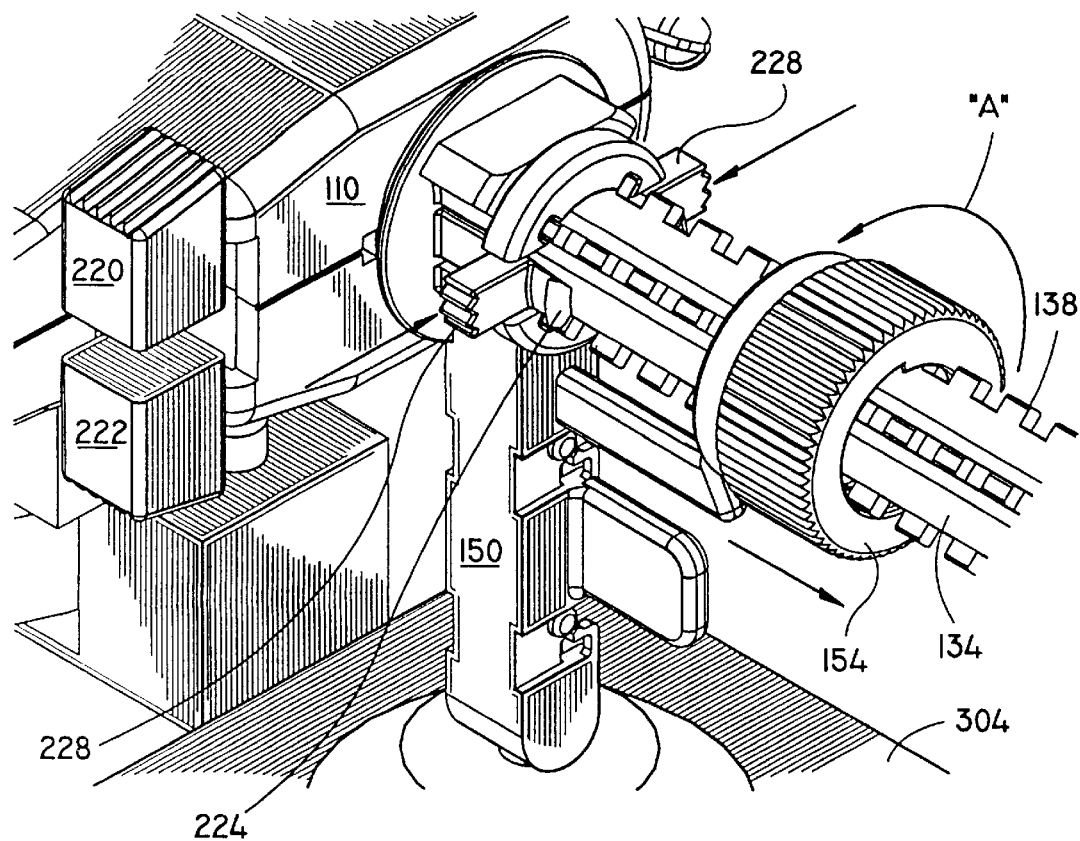
FIG. 26 is a partial perspective view showing operational features of a tissue localization subassembly.

The breast is then imaged by known stereotactic imaging capabilities to determine the three-dimensional, i.e., x, y, and z axis coordinates of the target tissue. As shown in FIG. 26, locking tabs 224 which are formed on flexible fingers 226 are biased inwardly toward each other by applying pressure to release buttons 228. The surgeon makes an appropriately sized skin incision to accommodate tubular body portion 116 and dissects toward the target tissue. Insertion depth adjusting knob 154 is rotated counterclockwise as indicated by arrow "A" in FIG. 26 until the distal end of knob traverses a distance measured by markings (FIG. 6) formed on needle advancing shaft. This distance represents a "z" axis distance which corresponds to the insertion depth required as calculated from the "z" distance to the target tissue, which is displayed by the stereotactic machine.

Figure 27:
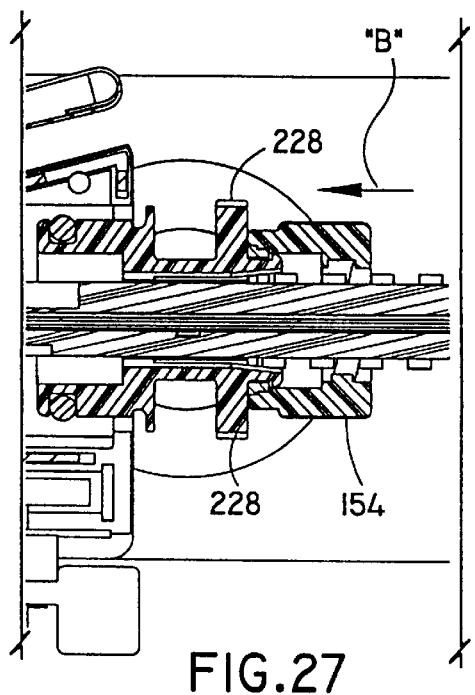
FIG. 27 is a cross-sectional view of the tissue localization subassembly of FIG. 26.
Figure 28:
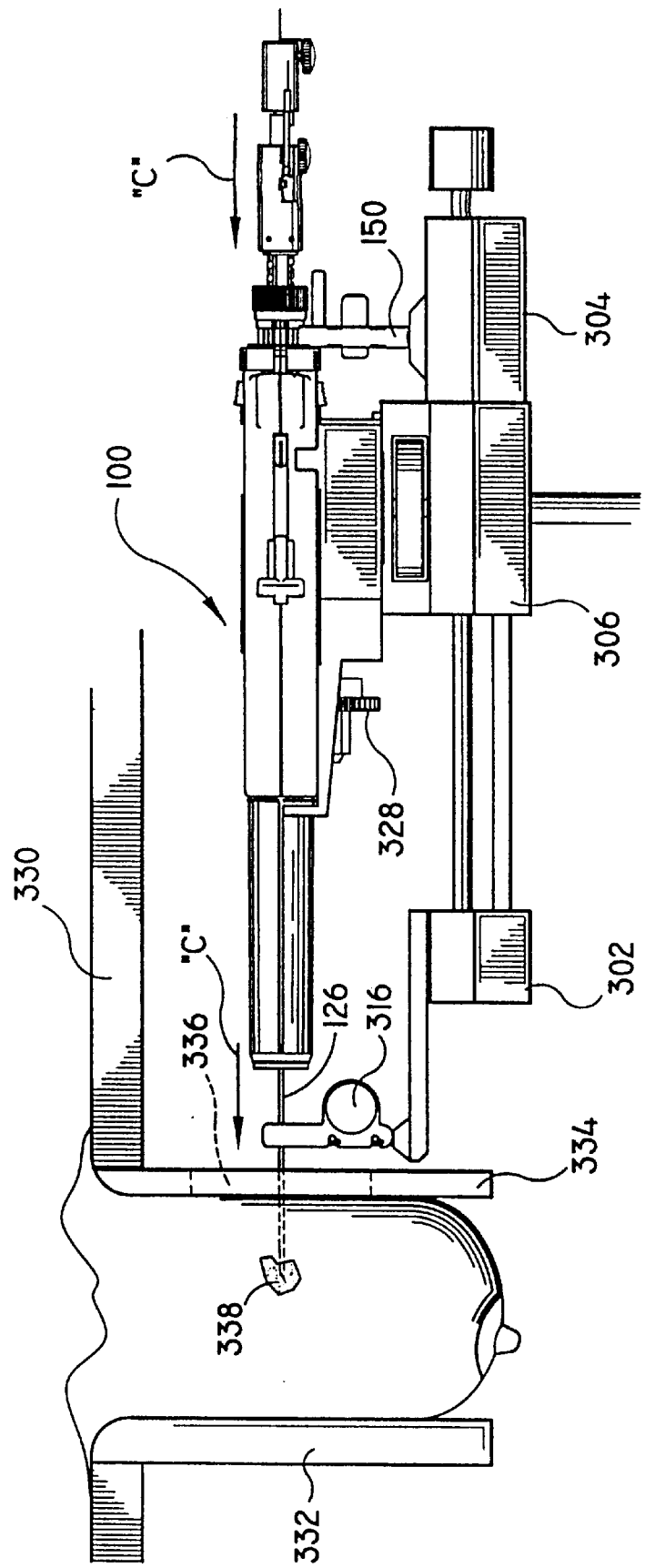
FIG. 28 is a sequential operational side view, similar to FIG. 25, showing the instrument in use.

As shown in FIGS. 27 and 28, localization needle 126 is driven into the breast by manually pushing tissue localizing subassembly 118 distally in the direction indicated by arrows "B" and "C" in FIGS. 27 and 28, respectively. As shown in FIG. 27, locking tabs 224 will function to lock insertion depth adjusting knob 154 fixed relative to fixed end block 304 of the stereotactic machine. Thus, further longitudinal movement of tissue marking subassembly 118 is prevented with respect to the pendulant breast once the localization needle 126 is in place at the x, y, and z axis coordinates of target tissue 338. Alternatively, adjusting knob 154 can be rotated with locking tabs 224 locked in place so that localization needle 126 advances due to the threading action of knob 154 urging needle advancing shaft 134 in a distal direction.

The patient's breast is then imaged again, e.g., by x-ray to determine that localization needle 126 has in fact been inserted to the proper "z" depth. Once the proper depth is confirmed, tissue marker is deployed as illustrated in FIGS. 29–36. In the initial position of marker deployment mechanism 155, as shown in FIGS. 29 and 23, set screw 164 is advanced to impinge cable 130 between clip 162 and the inner surface of a bore through cable anchor 160. Slide member 158 is positioned in its distal-most location which corresponds to a fully retracted position of advancing tube 132 (FIG. 19).

Figure 31:
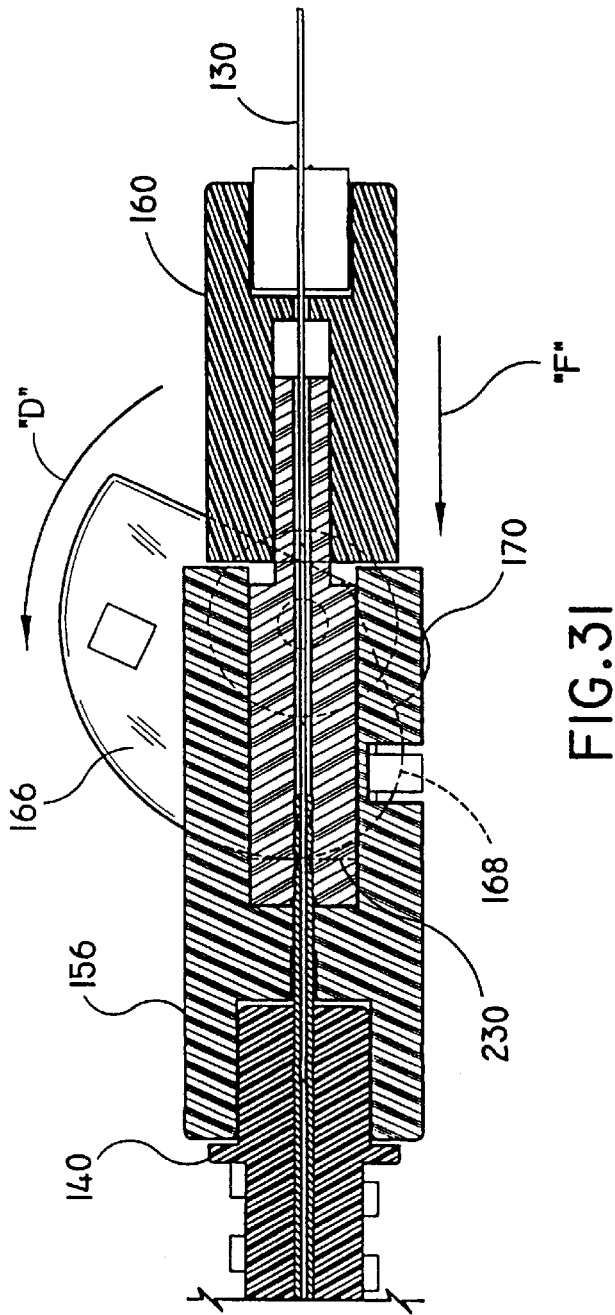
FIG. 31 is a further partial cross-sectional view, similar to FIG. 30, showing rotation of a marker deployment actuator to effect deployment of the tissue marker.
Figure 32:
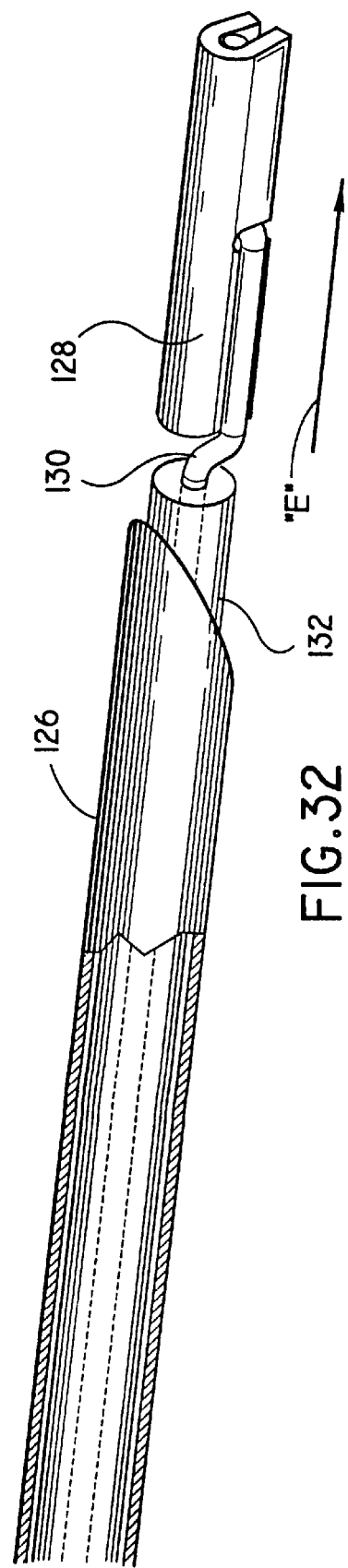
FIG. 32 is a partial perspective view showing the marker exiting from the distal end of a localization needle.

Marker 128, cable 130 and advancing tube 132 are all advanced distally from the end of localization needle 126, as indicated by arrow "E" in FIG. 32, by rotating cam 166 counterclockwise when viewed from the perspective of FIG. 31 in the direction of arrow "D". Cam surface 168 thereby urges biasing surface 230 (best shown in FIG. 29) of slide member 158 in a distal direction as indicated by arrow "F" in FIG. 31.

Rotation of marker 128 into its substantially perpendicular deployed position relative to advancing tube 132, is achieved by continued rotation of cam 166 in a counterclockwise direction as viewed from the perspective of FIG. 33, in the direction of arrow "G". This motion causes cam surface 170 to urge cable anchor 160 to move distally relative to actuator housing member 156 in the direction of arrow "H" and, therefore, cable 130 to move distally as indicated by arrow "I" in FIG. 34. Upon full rotation of cam 166, marker 128 is rotated into its substantially perpendicular position as shown in FIGS. 35 and 36.

Figure 37:
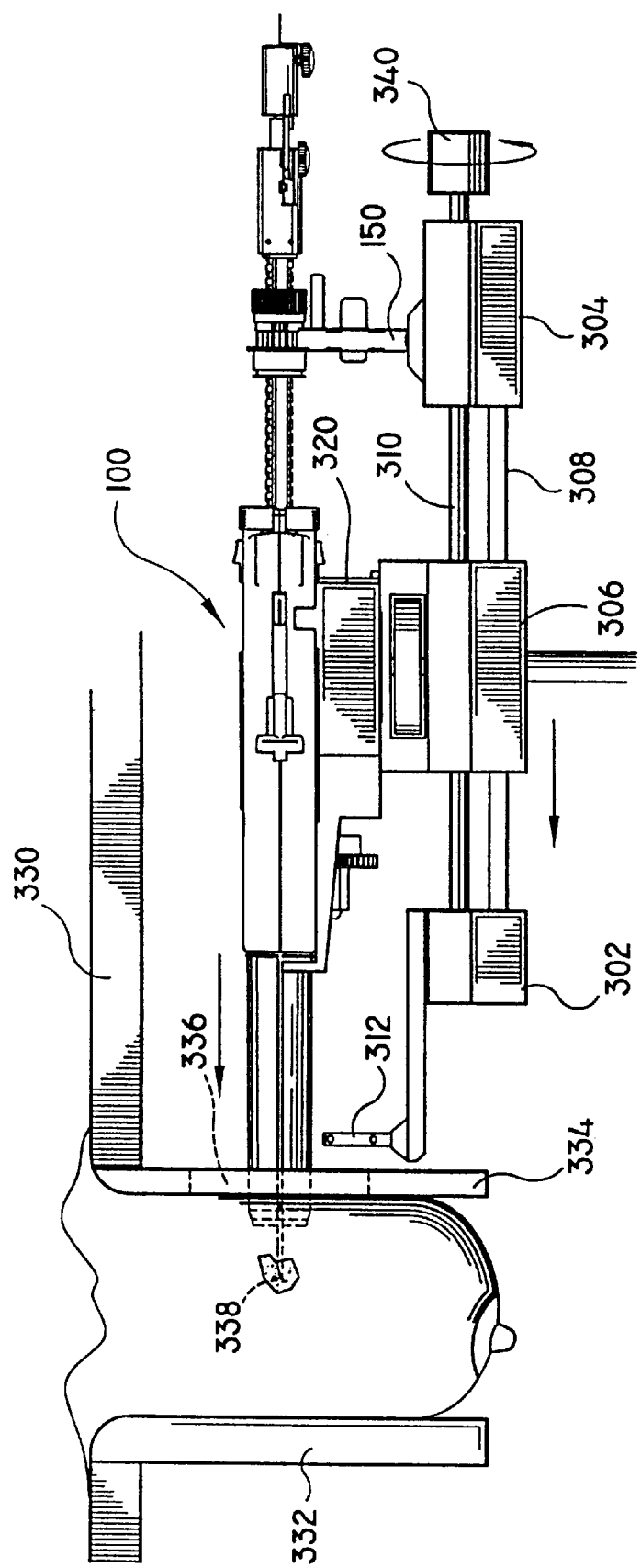
FIG. 37 is a further sequential operational side view of the instrument in use.
Figure 38:
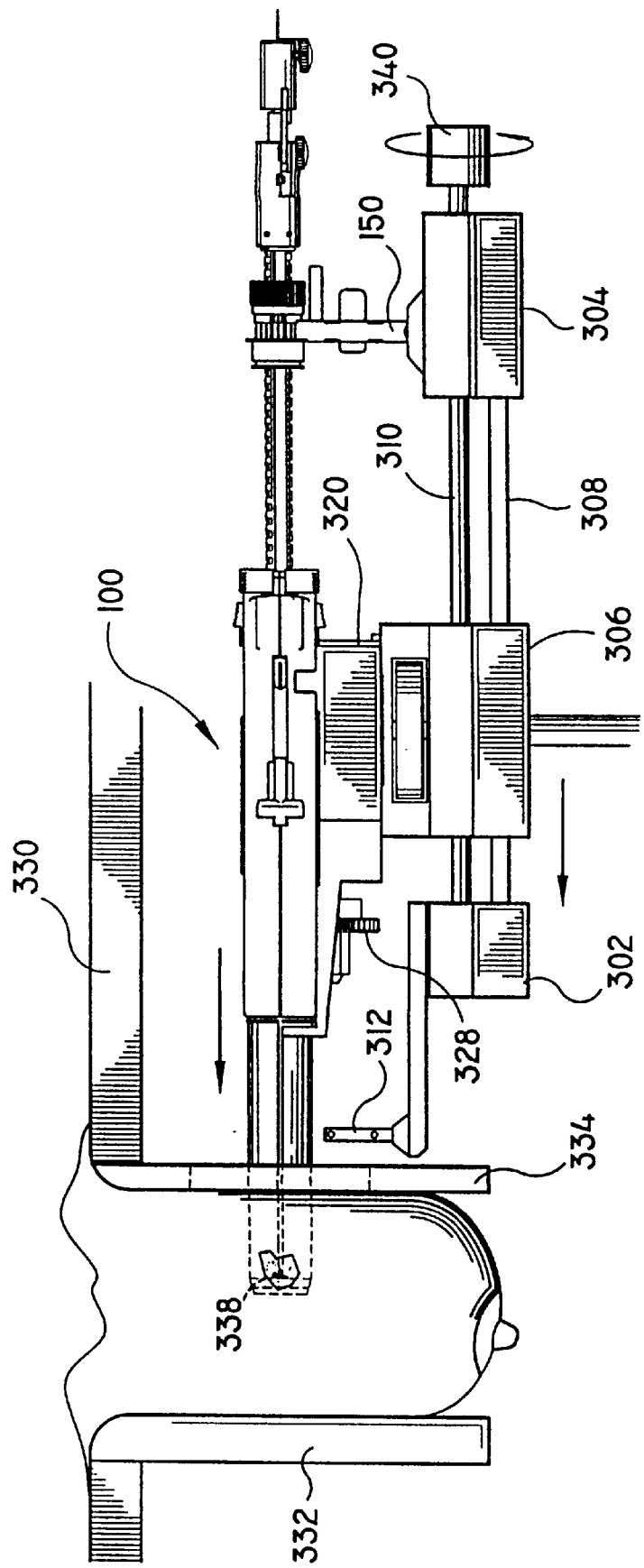
FIG. 38 is a further sequential operational side view of the instrument in use.

When marker 128 has been fully deployed as shown in FIG. 36, the patient's breast is then preferably imaged again, e.g. by x-ray, to verify that the marker 128 has properly deployed. Once marker deployment is confirmed, needle guide 316 is removed. The stereotactic drive motor (not shown) is turned on to rotate coring cannula 188. Alternatively, coring cannula may be manually rotated, for example, by connecting a rack to mesh with teeth 198 (FIG. 20) of coring cannula 188. Control knob 340 is rotated as shown in FIG. 37 to advance instrument stage 306 distally thereby causing coring cannula to simultaneously rotate and advance distally to core a sample of tissue surrounding the target tissue as shown in FIG. 38.

Figure 42:
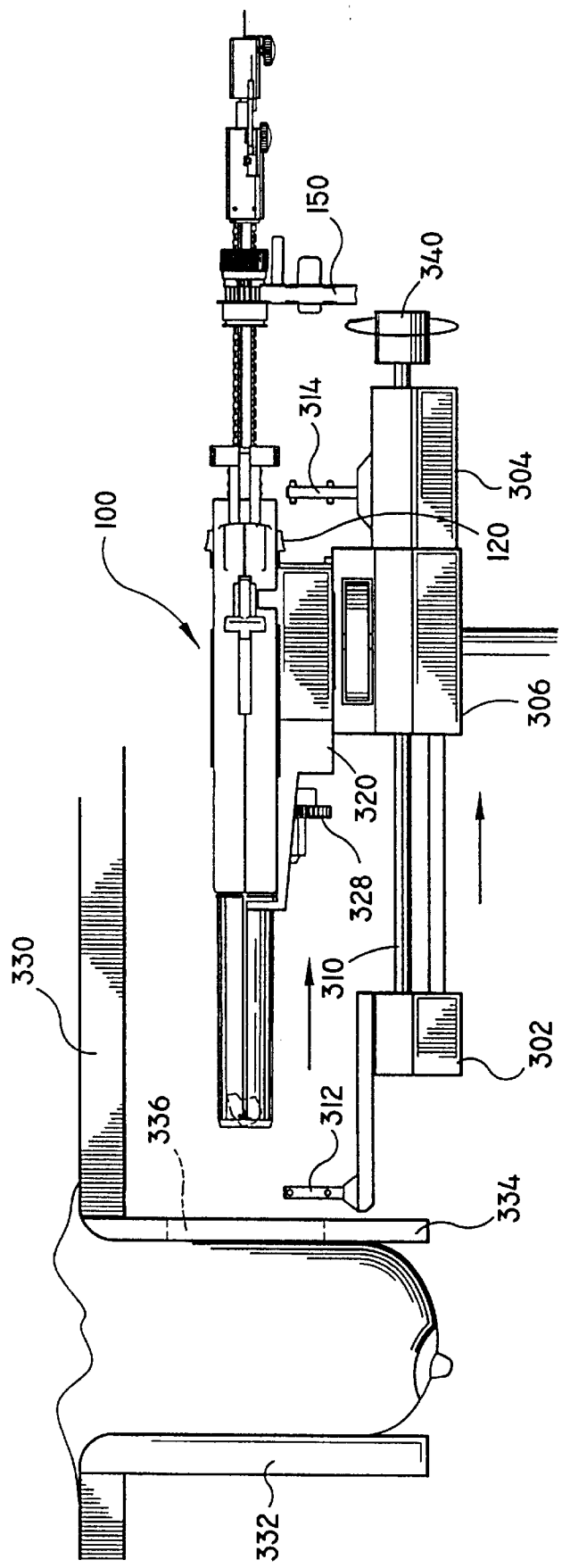
FIG. 42 is a further is a further sequential operational side view of the instrument in use.
Figure 43:
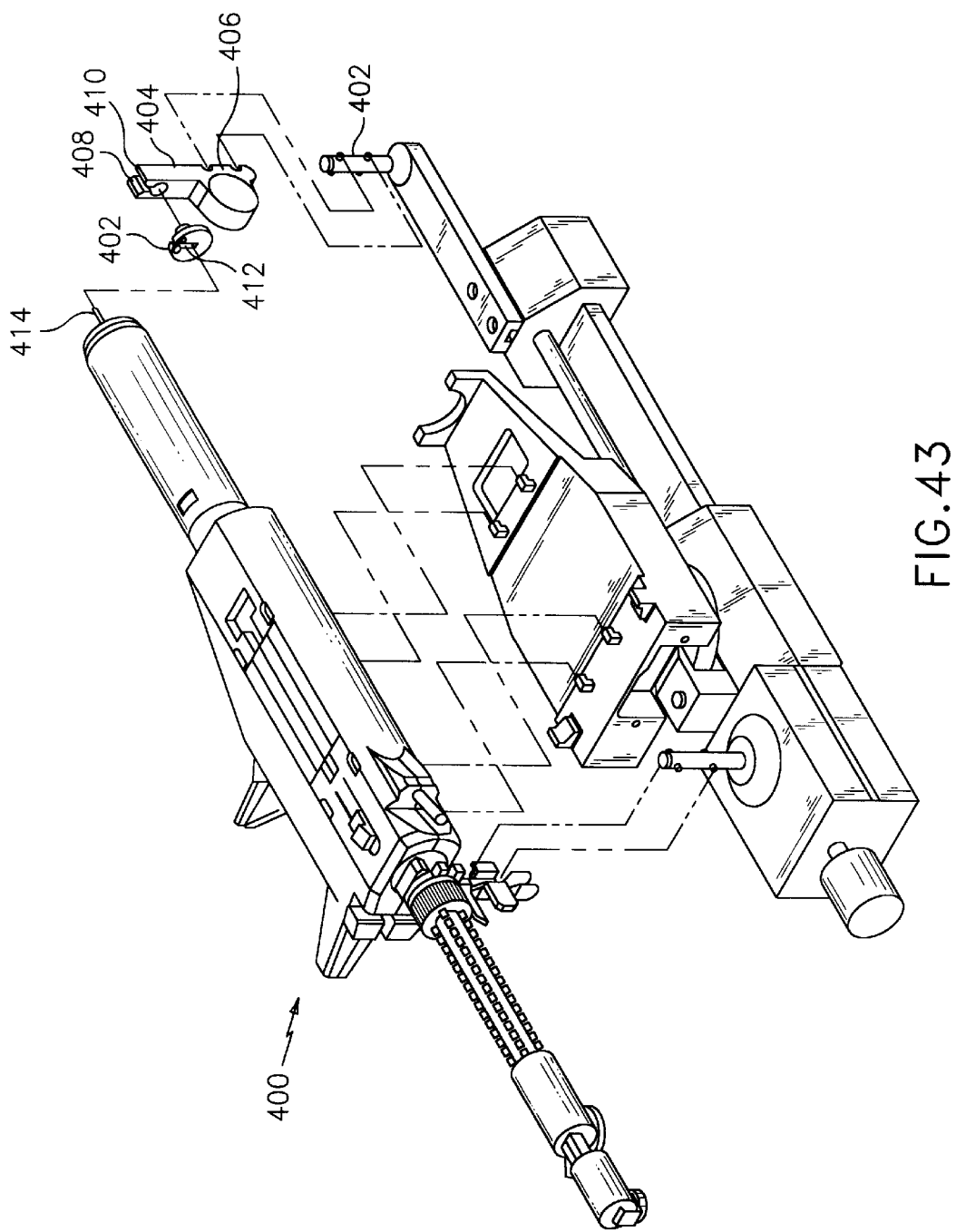
FIG. 43 is a perspective view with parts separated of an alternative embodiment of a tissue localizing and removing instrument.

Referring to FIGS. 39–42, with instrument 100 advanced by rotation of control knob 340 to the previously calculated "z" dimension depth, release buttons 222 are urged toward each other to release stops 212 (FIG. 22) from biasing against the inner surface of the distal end wall of housing 110. Slide 210 is then pulled proximally, thereby retracting coring cannula 188 as shown in FIG. 40. When slide 210 is retracted, actuation of trigger 200 is enabled. Movement of trigger 200 proximally causes cutting wire 178 to be pulled proximally through conduit 184. Loop 180 is thereby pulled transversely across the open distal end of elongated tubular body 116 to sever the tissue core from the surrounding tissue. During this actuation of cutting wire 184, electrocautery may also be applied as desired to effectuate additional cutting action of the tissue. As shown in FIG. 42, instrument 100 is then backed out of the breast by rotating control knob 340 in reverse direction as that used to advance the instrument. Instrument 100 is thereafter removed from platform 320 by depressing flexible finger 120 and sliding the instrument off of hooks 318.

Referring to 43, an alternative embodiment is shown as instrument 400. A post 402 provides a mounting surface for a needle guide 404 which is preferably provided in the same packaging along with the instrument 400. Needle guide 404 attaches readily to post 402, e.g., by snap fitting onto the post on attachment end portion 406. Needle guide 404 defines a needle receiving channel 408 on a first end portion 410 opposite attachment end portion 406. A needle locking member 412 attaches to needle guide 404 to secure a needle 414 during a biopsy procedure.

Figure 44:
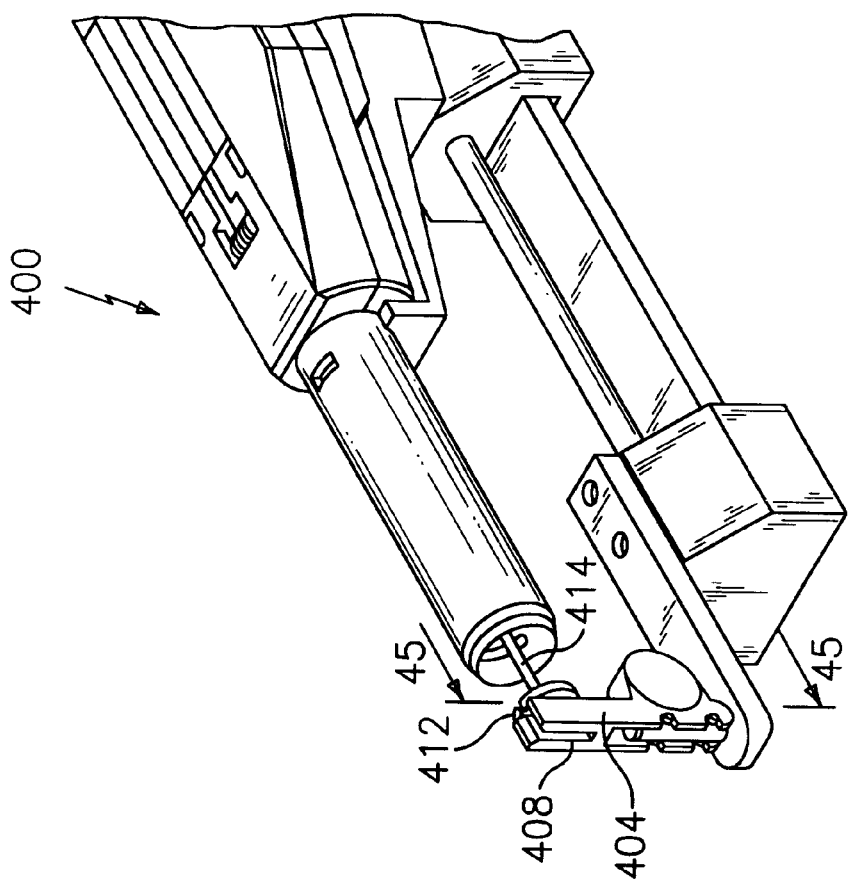
FIG. 44 is a partial perspective view of the tissue localizing and removing instrument.

Referring to FIG. 44, needle guide 404 is shown mounted on post 402. During a biopsy procedure, needle guide 404 supports needle 414 within channel 408. Needle locking member 412 permits needle 414 to extend therethrough.

Figure 46:
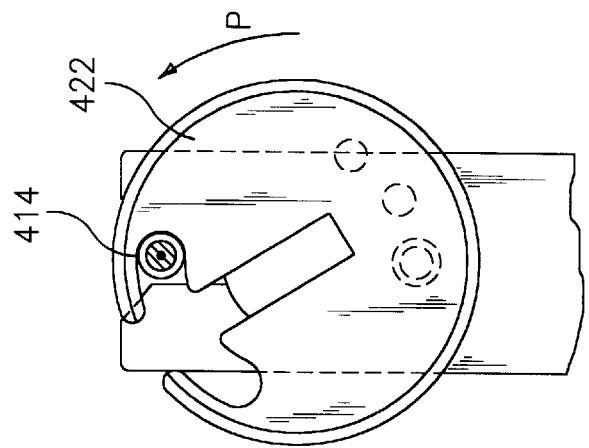
FIG. 46 is a front view of the locking member of FIG. 44 in a needle locking position.
Figure 45:
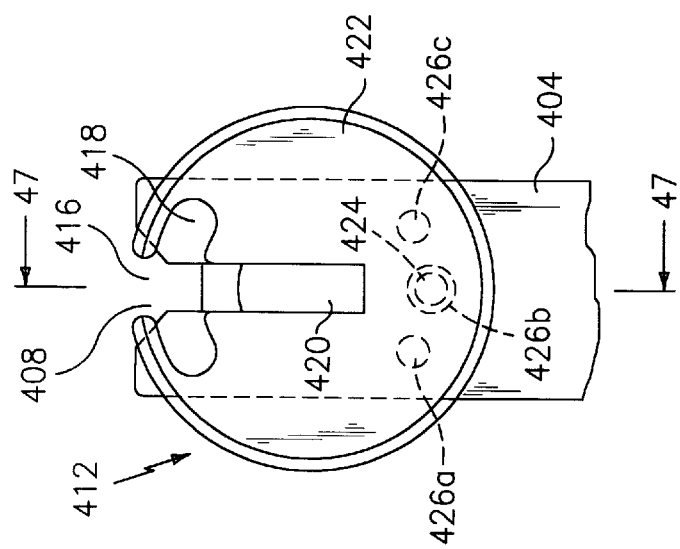
FIG. 45 is a front view taken along section line 45—45 of FIG. 44 showing a locking member in a needle receiving position.

Referring to FIGS. 45 and 46, needle locking member 412 includes a needle lock 422. Needle lock 422 defines an opening 416 therethrough dimensioned and configured to receive needle 414 longitudinally therein. Opening 416 includes an arcuate shaped opening 418 in communication about its axis of symmetry with a slot 420 centrally disposed on the axis of symmetry of arcuate shaped opening 418. Needle lock 422 rotatably attaches to needle guide 404 such that arcuate shaped opening 418 and channel 408 communicate to allow needle to longitudinally extend therethrough. A pin 424 (shown in hidden dashed lines) extends from needle guide 404 to engage one of a plurality of holes 426 to secure needle lock in its operative positions.

Each hole corresponds to a different position of needle lock 422. Hole 426b corresponds to a needle receiving position. Needle 414 may be lowered into channel 408. Needle lock 422 is now rotated in the direction of arrow "P" to secure needle 414 and prevent needle 414 from exiting channel 408. In this position, pin 426 is engages hole 426a. Arcuate shaped opening 418 is radially disposed on needle lock 422 such that needle 414 remains within arcuate shaped opening 418 during the rotation of needle lock 422. Alternately, needle lock 422 may be rotated opposite arrow "P" such that needle 414 is locked on the opposite side of arcuate shaped opening 418 and pin 424 is secured within a hole 426c.

Figure 47:
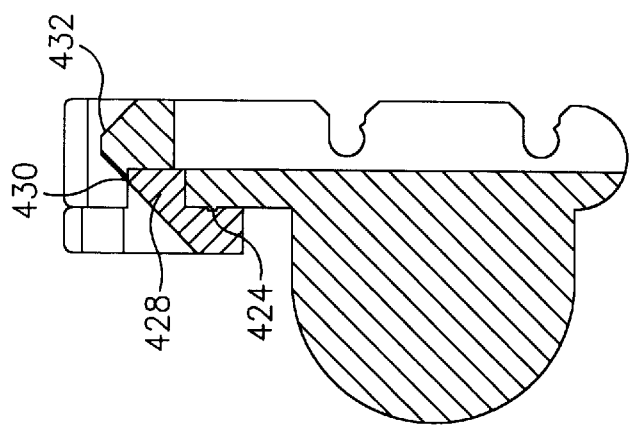
FIG. 47 is a cross-sectional view taken along section line 47—47 of FIG. 45.

Referring to FIG. 47, a peg portion 428 of needle lock 422 is received within an opening 430 in needle guide 404 to enable rotation of needle lock 422. Channel 408 has a support surface 432 therein for engaging needle 414 during operation.

It will be understood that various modifications may be made to the embodiment disclosed herein. Therefore, the above description should not be construed as limiting, but merely as exemplifications of a preferred embodiment. Those skilled in the art will envision other modifications within the scope and spirit of the claims appended hereto.

What is claimed is:

1. A surgical apparatus for securing a needle extending therethrough, which comprises:

a post having a channel therein mounted to a base, the post positioned in operative alignment with a needle mounted on the base; and a locking member associated with the post in operative alignment with the needle, the locking member defining an opening therethrough to receive the needle, the locking member operable between a needle receiving position wherein the needle may be inserted or removed from the locking member and a needle retaining position wherein the needle is retained in at least one direction of movement.

2. A surgical apparatus for securing a needle extending therethrough as recited in claim 1, further comprises a needle guide member which is connected to the post and defines a support surface which supports the locking member therein.

3. A surgical apparatus for securing a needle extending therethrough as recited in claim 2, wherein the locking member is rotatably supported by the needle guide member.

4. A surgical apparatus for securing a needle extending therethrough as recited in claim 1, wherein the post has a pin extending therefrom and the needle guide member has a plurality of holes configured and dimensioned to receive the pin wherein at least one of the plurality of holes corresponds to the needle receiving position and at least one of the plurality of holes corresponds to the needle locking position.

5. A surgical apparatus for securing a needle extending therethrough as recited in claim 1, wherein the opening is arcuate-shaped and is disposed at a constant radial distance from a center of rotation point on the locking member.

6. A surgical apparatus for localizing and removing tissue, which comprises:

a tissue cutting member mounted on a base and defining an opening near a distal end, the tissue cutting member further forming a tissue receiving cavity in communication with the opening;

a needle disposed within the cavity and defining a longitudinal passageway therethrough;

a post mounted on the base; and a locking member mounted on the post and defining having a needle receiving opening in operative alignment with the needle, the locking member being operable between a needle receiving position wherein the needle may be inserted or removed from the locking member and a needle retaining position wherein the needle is retained in at least one direction of movement.

7. A surgical apparatus for localizing and removing tissue as recited in claim 6, further comprises a needle guide member which is connected to the post and defines a support surface which supports the locking member therein.

8. A surgical apparatus for localizing and removing tissue as recited in claim 7, wherein the locking member is rotatably supported by the needle guide member.

9. A surgical apparatus for localizing and removing tissue as recited in claim 6, further comprises a tissue marker disposed within the longitudinal passageway.

10. A surgical apparatus for localizing and removing tissue as recited in claim 9, further comprises a marker deploying mechanism operatively connected to the marker.

11. A surgical apparatus for localizing and removing tissue as recited in claim 6, wherein the post has a pin extending therefrom and the locking member has a plurality of holes configured and dimensioned to receive the pin wherein at least one of the plurality of holes corresponds to the needle receiving position and at least one of the plurality of holes corresponds to the needle retaining position.

12. A surgical apparatus as recited in claim 6, wherein the needle receiving opening is arcuate-shaped and is disposed at a constant radial distance from a center of rotation point on the locking member.

13. A method for surgically localizing and removing tissue, comprising the steps of:

a) providing a tissue cutting member mounted on a base and defining an opening near a distal end, the tissue cutting member further forming a tissue receiving cavity in communication with the opening, a needle disposed within the cavity and defining a longitudinal passageway therethrough, a post mounted on the base and a locking member mounted on the post and defining a needle receiving opening in operative alignment with the needle, the locking member being operable between a needle receiving position wherein the needle may be inserted or removed from the locking member and a needle retaining position wherein the needle is retained in at least one direction of movement;

b) locking the needle within the locking member by rotating the locking member into the needle retaining position;

c) positioning the needle within target tissue;

d) severing the tissue to be removed; and e) removing the severed tissue from a patient.

14. A method for surgically localizing and removing tissue according to claim 13, wherein the step of positioning the needle includes advancing the needle relative to the tissue cutting member in a direction toward the target tissue.

15. A method for surgically localizing and removing tissue according to claim 13, further comprising the step of mounting the base on an instrument guidance system which includes a movable instrument platform.

16. A method for surgically localizing and removing tissue according to claim 13, further comprising a marker disposed within the longitudinal passageway and further comprising the step of deploying the marker to mark the target tissue.

* * * * *